US007927529B2

(12) United States Patent
Dave

(10) Patent No.: US 7,927,529 B2
(45) Date of Patent: Apr. 19, 2011

(54) METHOD OF FORMING BIOABSORBABLE DRUG DELIVERY DEVICES

(75) Inventor: Vipul Bhupendra Dave, Hillsborough, NJ (US)

(73) Assignee: Cordis Corporation, Miami Lakes, FL (US)

( * ) Notice: Subject to any disclaimer, the term of this patent is extended or adjusted under 35 U.S.C. 154(b) by 8 days.

(21) Appl. No.: 12/244,622

(22) Filed: Oct. 2, 2008

(65) Prior Publication Data

US 2009/0026650 A1 Jan. 29, 2009

Related U.S. Application Data

(62) Division of application No. 11/327,700, filed on Jan. 6, 2006.

(51) Int. Cl.
*B29C 47/04* (2006.01)

(52) U.S. Cl. .................. 264/171.26; 264/209.1; 264/211

(58) Field of Classification Search ............. 264/171.26, 264/209.1, 211
See application file for complete search history.

(56) References Cited

U.S. PATENT DOCUMENTS

| 4,553,545 A | 11/1985 | Maass et al. |
| 5,085,629 A | 2/1992 | Goldberg et al. |
| 5,171,812 A | 12/1992 | Domb |
| 5,423,885 A | 6/1995 | Williams |
| 5,464,450 A | 11/1995 | Buscemi et al. |
| 5,670,161 A | 9/1997 | Healy et al. |
| 5,709,713 A | 1/1998 | Evans et al. |
| 5,954,744 A | 9/1999 | Phan et al. |
| 6,039,755 A | 3/2000 | Edwin et al. |
| 6,080,177 A | 6/2000 | Igaki et al. |
| 6,156,062 A | 12/2000 | McGuinness |
| 6,174,330 B1 | 1/2001 | Stinson |
| 6,203,569 B1 | 3/2001 | Wijay |
| 6,423,091 B1 | 7/2002 | Hojeibane |
| 6,425,915 B1 | 7/2002 | Khosravi et al. |
| 6,524,334 B1 | 2/2003 | Thompson |

(Continued)

FOREIGN PATENT DOCUMENTS

EP 1555278 A1 1/2004

(Continued)

OTHER PUBLICATIONS

"Blend" Sensagent Dictionary. Date accessed Oct. 7, 2010. http://dictionary.sensagent.com/blend/en-en/.

*Primary Examiner* — Joseph S Del Sole
*Assistant Examiner* — James Sanders

(57) ABSTRACT

A bioabsorbable drug delivery device and various methods of making the same. The devices are preferably formed from bioabsorbable materials using low temperature fabrication processes, hereby drugs or other bio-active agents are incorporated into or onto the device and degradation of the drugs or other agents during processing is minimized. Radiopaque markers may also be incorporated into, or onto, the devices. The devices may be generally tubular helical stents comprised of a solid ladder or an open lattice configuration, or a hybrid combination thereof. The tubular helical stents are generally formed from precursor fibers, films or tubes. The solid ladder configuration provides increased radiopacity and increased radial strength, whereas the open lattice configuration provides better endothelialization and fluid flow through the stent. The drug or other agent delivery capacity of the devices may provide local or regionalized drug or other agent delivery, or a combination thereof, with more consistent concentrations of drugs or other agents delivered from the device to the treatment site along the entire length of the device.

13 Claims, 9 Drawing Sheets

U.S. PATENT DOCUMENTS

| | | |
|---|---|---|
| 6,533,809 B2 | 3/2003 | Von Oepen |
| 6,602,281 B1 | 8/2003 | Klein |
| 6,626,939 B1 | 9/2003 | Burnside et al. |
| 6,730,116 B1 | 5/2004 | Wolinsky et al. |
| 6,736,842 B2 | 5/2004 | Healy et al. |
| 6,743,388 B2 | 6/2004 | Sridharan et al. |
| 6,824,559 B2 | 11/2004 | Michal |
| RE38,711 E | 3/2005 | Igaki et al. |
| 6,932,930 B2 | 8/2005 | DeSimone et al. |
| 6,991,647 B2 | 1/2006 | Jadhav |
| 6,997,948 B2 | 2/2006 | Stinson |
| 7,014,654 B2 | 3/2006 | Welsh et al. |
| 7,128,862 B2 | 10/2006 | Wang |
| 2002/0188346 A1 | 12/2002 | Healey et al. |
| 2003/0060874 A1 | 3/2003 | Igaki |
| 2003/0083732 A1 | 5/2003 | Stinson |
| 2003/0125802 A1 | 7/2003 | Callol et al. |
| 2003/0208259 A1 | 11/2003 | Penhasi |
| 2003/0216806 A1 | 11/2003 | Togawa et al. |
| 2004/0006382 A1 | 1/2004 | Sohier |
| 2004/0024448 A1 | 2/2004 | Chang et al. |
| 2004/0056384 A1 | 3/2004 | Hill et al. |
| 2004/0088044 A1 | 5/2004 | Brown et al. |
| 2004/0098095 A1 | 5/2004 | Burnside et al. |
| 2004/0117007 A1 | 6/2004 | Whitbourne et al. |
| 2004/0131808 A1 | 7/2004 | Schoenle et al. |
| 2004/0148014 A1 | 7/2004 | Nuutinen et al. |
| 2004/0167615 A1 | 8/2004 | Lenz |
| 2004/0176834 A1 | 9/2004 | Brown et al. |
| 2004/0193241 A1 | 9/2004 | Stinson |
| 2004/0215330 A1 | 10/2004 | Igaki |
| 2004/0247775 A1 * | 12/2004 | Boulais et al. .................. 427/2.1 |
| 2004/0249441 A1 * | 12/2004 | Miller et al. .................. 623/1.15 |
| 2004/0249450 A1 | 12/2004 | Ishii |
| 2004/0260386 A1 | 12/2004 | Shalaby |
| 2005/0010275 A1 * | 1/2005 | Sahatjian et al. ............. 623/1.11 |
| 2005/0021131 A1 | 1/2005 | Venkatraman et al. |
| 2005/0036945 A1 | 2/2005 | Thomas et al. |
| 2005/0123582 A1 | 6/2005 | Sung et al. |
| 2005/0137678 A1 | 6/2005 | Varma |
| 2005/0149172 A1 | 7/2005 | Varma |
| 2005/0163821 A1 | 7/2005 | Sung et al. |
| 2005/0187615 A1 | 8/2005 | Williams et al. |
| 2005/0216074 A1 | 9/2005 | Shatjian et al. |
| 2005/0228492 A1 | 10/2005 | DeSimone et al. |
| 2005/0261760 A1 | 11/2005 | Weber |
| 2006/0020330 A1 | 1/2006 | Huang et al. |
| 2006/0034769 A1 | 2/2006 | Kohn et al. |
| 2006/0036316 A1 | 2/2006 | Zeltinger et al. |
| 2006/0076708 A1 | 4/2006 | Huang et al. |
| 2006/0079955 A1 | 4/2006 | Brown |
| 2006/0129222 A1 | 6/2006 | Stinson |
| 2006/0134211 A1 | 6/2006 | Lien et al. |
| 2006/0177480 A1 | 8/2006 | Sung et al. |
| 2006/0229711 A1 | 10/2006 | Yan et al. |
| 2007/0283552 A1 | 12/2007 | Gale et al. |
| 2007/0290412 A1 | 12/2007 | Capek et al. |
| 2007/0293938 A1 | 12/2007 | Gale et al. |
| 2009/0096137 A1 | 4/2009 | Williams et al. |

FOREIGN PATENT DOCUMENTS

| | | |
|---|---|---|
| WO | WO 98/41170 A1 | 9/1998 |

* cited by examiner

METHOD OF FORMING BIOABSORBABLE DRUG DELIVERY DEVICES

CROSS REFERENCE TO RELATED APPLICATION

This application is a divisional application of U.S. application Ser. No. 11/327,700 filed on Jan. 6, 2006 and claims priority thereto under 35 U.S.C. 121.

BACKGROUND OF THE INVENTION

1. Field of the Invention

The invention generally relates to bioabsorbable drug delivery devices and methods of making the same. More specifically, the invention relates to drug delivery devices comprised of bioabsorbable materials formed into desired geometries by different polymer processing methods.

2. Related Art

Intraluminal endovascular stents are well-known. Such stents are often used for repairing blood vessels narrowed or occluded by disease, for example, or for use within other body passageways or ducts. Typically the stent is percutaneously routed to a treatment site and expanded to maintain or restore the patency of the blood vessel or other passageway or duct within which the stent is placed. The stent may be a self-expanding stent comprised of materials that expand after insertion according to the body temperature of the patient, or the stent may be expandable by an outwardly directed radial force from a balloon, for example, whereby the force from the balloon is exerted on an inner surface of the stent to expand the stent towards an inner surface of the vessel or other passageway or duct within which the stent is placed. Ideally, once placed within the vessel, passageway or duct, the stent will conform to the contours and functions of the blood vessel, passageway or duct in which the stent is deployed.

Moreover, as in U.S. Pat. No. 5,464,450, stents are known to be comprised of biodegradable materials, whereby the main body of the stent degrades in a predictably controlled manner. Stents of this type may further comprise drugs or other biologically active agents that are contained within the biodegradable materials. Thus, the drugs or other agents are released as the biodegradable materials of the stent degrade.

Although such drug containing biodegradable stents, as described in U.S. Pat. No. 5,464,450, may be formed by mixing or solubilizing the drugs with the biodegradable polymer comprising the stent, by dispersing the drug into the polymer during extrusion of the polymer, or by coating the drug onto an already formed film or fiber, such stents typically include relatively small amounts of drugs. For example, U.S. Pat. No. 5,464,450 contemplates containing only up to 5% aspirin or heparin in its stent for delivery therefrom. Moreover, the profile of drugs delivered from such stents tend to concentrate the drugs at a primary region of the stent rather than delivering drugs more uniformly along a length of the stent. Lengthwise delivery of drugs from a stent could enhance treatment of a targeted site, disease or condition. Further, such stents as disclosed in U.S. Pat. No. 5,464,450 are often made without radiopaque markers. The omission of radiopaque markers inhibit the visualization and accurate placement of the stent by the medical practitioner. Further still, stents produced by melt-spinning a polymer into fibers containing drugs in accordance with U.S. Pat. No. 5,464,450 tend to stretch the fibers as monofilaments at temperatures of 500-200° C. This process suggests the drugs incorporated into the stents are stable at high temperatures. Because relatively few high temperature stable drugs exist, this limits polymer processing options significantly for stents or other drug delivery devices.

Polymers are often processed in melt conditions and at temperatures that may be higher than is conducive to the stability of the drugs or other agents to be incorporated into a bioabsorbable drug delivery device. Typical methods of preparing biodegradable polymeric drug delivery devices, such as stents, include fiber spinning, film or tube extrusion or injection molding. All of these methods tend to use processing temperatures that are higher than the melting temperature of the polymers. Moreover, most bioabsorbable polymers melt process at temperatures at which most drugs are not stable and tend to degrade.

Stents of different geometries are also known. For example, stents such as disclosed in U.S. Pat. No. 6,423,091 are known to comprise a helical pattern comprised of a tubular member having a plurality of longitudinal struts with opposed ends. Such helical patterned stents typically have adjacent struts connected to one another via the ends. The pitch, or angle, of the longitudinal struts as it wraps around the tubular stent in the helical configuration is typically limited, however, by the manner in which the longitudinal struts are made. Limiting the pitch or angle of the longitudinal struts of such helical stents can adversely affect the radial strength of such stents.

In view of the above, a need exists for systems and methods that form implantable bioabsorbable polymeric drug delivery devices with desired geometries or patterns, wherein the devices have increased and more effective drug delivery capacity and radiopacity. Further in view of the above, a need exists for systems and methods wherein degradation of the drugs incorporated into the devices during processing is minimized. Still further in view of the above, a need exists for systems and methods that form the bioabsorbable devices into geometries having improved radial strength and variable strut pitch capabilities and configurations, and having increased and more effective drug delivery capacity and radiopacity.

SUMMARY OF THE INVENTION

The systems and methods of the invention provide bioabsorbable polymeric drug delivery devices with increased and more effective drug delivery capacity and increased radiopacity.

According to the systems and methods of the invention, the devices are preferably formed from bioabsorbable polymers using low temperature fabrication processes. Preferred low temperature processes for preparing different structures such as films, fibers and tubes include solution processing and extrusion, melt processing using solvents and plasticizers, processing from gels and viscous solutions, and super-critical fluid processing, whereby drugs that are not stable at high temperatures are able to be incorporated into the polymer forming the device. Different processing methods can further include solvent extraction, coating, co-extrusion, wire-coating, lyophilization, spinning disk, wet and dry fiber spinning, electrostatic fiber spinning, and other processing methods known in the art. The preferred low temperature processes increases the number or concentration of drugs or other agents that may be incorporated into the drug delivery devices made according to the systems and methods of the invention. For drugs with high temperature stability, a variety of high temperature melt processing methods, including extrusion, co-extrusion, fiber spinning, injection molding, and compression molding may also be used to form the devices according to the invention. Different geometries and performance characteristics of the drug delivery devices are achieved according to the different processes and materials used to make the devices.

In some embodiments, the drug delivery device is a stent comprised of bioabsorbable polymers with drugs or other bio-active agents and radiopaque markers incorporated therein. The drugs or other bio-active agents are incorporated into, or coated onto, the stent in significantly greater amounts than in prior art stents. Likewise, radiopaque markers may be provided in or on the stent. The combination of greater amounts of drugs, or other agents, for delivery from the device with the radiopaque markers tends to improve the treatment of a targeted site, disease or condition and the visualization and placement of the device in the patient.

In a preferred embodiment, the drug delivery device is a stent comprised either of a tubular or a helical configuration wherein the radiopacity, radial strength, flexibility and other performance attributes of the device are optimized by different design parameters. In the case of a helical configuration, radial strength of the stent tends to be increased by a generally solid ladder configuration. Alternatively, endothelialization of the device and flow therethrough is increased by a generally open lattice structure with high surface area. Hybrid designs combining the solid ladder with the open lattice structure provides aspects of increased radial strength and improved endothelialization and flow therethrough. The helical design also provides flexibility and bending properties to treat disease states in various anatomical regions such as the superior femoral artery or below the knee.

Other embodiments of the systems and methods of the invention comprise forming a non-stent device such as a ring, or wrap, drug delivery device. The ring, or wrap, is similarly comprised of bioabsorbable materials wherein drugs or other agents and radiopaque markers are incorporated therein. The bioabsorbable materials are similarly processed according to the various processes outlined above with respect to the formation of the stents but are shaped in the appropriate ring, or wrap, geometry or pattern as desired.

The bioabsorbable polymeric materials that comprise the stent or other device according to the systems and methods of the invention are chosen based on several factors, including degradation time, retention of the mechanical properties of the stent or other device during the active drug delivery phase of the device, and the ability of the bioabsorbable materials to be processed into different structures and via different methods. Other factors, including processing and material costs and availability, may also be considered.

The types of bioabsorbable polymers contemplated by the systems and methods of the invention include, but are not limited to, bulk or surface erosion polymers that are hydrophilic or hydrophobic, respectively, and combinations thereof. These polymers tend to help control the drug delivery aspects of the stent or other drug delivery device. Other bioabsorbable polymeric materials that may comprise the stent or other drug delivery device according to the systems and methods of the invention are shape memory polymers, polymer blends, and/or composites thereof that contribute to retaining the mechanical integrity of the device until drug delivery is completed.

Because polymers are generally not radiopaque, the bioabsorbable polymeric materials comprising the drug delivery device according to the systems and methods of the invention may include additives to enhance the radiopacity of the stent or other drug delivery device. Such radiopaque additives may include inorganic fillers, metal powders, metal alloys or other materials known or later developed in the art. Alternatively, the device may be coated with radiopaque material. The radiopaque additives or coatings may be applied uniformly throughout or over the stent or device, or may be applied only to designated sections of the stent or device as markers.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Figure 1:
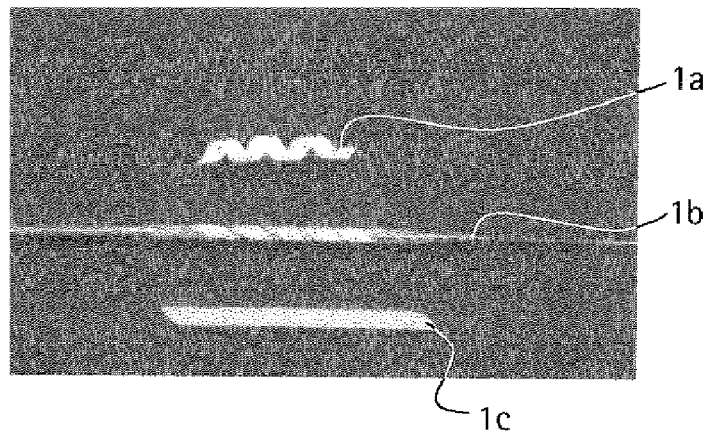
FIG. 1 illustrate a helical solid ladder stent in a deployed state, a balloon mounted state and in a film cut precursor state according to the systems and methods of the invention.

According to the systems and methods of the invention, a drug delivery device comprised of bioabsorbable materials is made by any of a variety of processes. The drug delivery devices can be prepared by solution-based processes using solvents as by, for example, fiber spinning (dry and wet spinning), electrostatic fiber spinning, spinning disk (thin films with uniform thickness), lyophilization, extrusion and co-extrusion, co-mingled fibers, supercritical fluids, solvent cast films, or solvent cast tubes, wherein low temperature processing is preferred. Alternatively, the drug delivery devices can be prepared by more conventional polymer processing methods in melt condition as by, for example, extrusion, co-extrusion, injection molding and compression molding. The artisan should readily appreciate the general techniques attendant with the various methods referred to above and, except as otherwise provided herein, detailed explanations thereof are omitted for brevity but understood to be included herein.

The processes used to prepare the drug delivery devices are preferably low temperature processes in order to minimize degradation of drugs or other bio-active agents that are incorporated into the matrix of bioabsorbable polymeric materials comprising the device. To this end, processing methods may comprise forming the device from bioabsorbable polymeric materials via low temperature, solution-based processes using solvents as outlined above and discussed in greater detail further below.

The drug delivery devices according to the systems and methods of the invention can be disease specific, and can be designed for local or regional therapy, or a combination thereof. The drugs or other agents delivered by the drug delivery devices according to the systems and methods of the invention may be one or more drugs, bio-active agents such as growth factors or other agents, or combinations thereof. The drugs or other agents of the device are ideally controllably released from the device, wherein the rate of release depends on either or both of the degradation rate of the bioabsorbable polymers comprising the device and the nature of the drugs or other agents. The rate of release can thus vary from minutes to years as desired. Surface erosion polymers or bulk erosion polymers, for example, can be used as the bioabsorbable polymer in order to better control the drug delivery therefrom.

Surface erosion polymers are typically hydrophobic with water labile linkages. Hydrolysis tends to occur fast on the surface of such surface erosion polymers with no water penetration in bulk. The drug release rate from devices comprised of such surface erosion polymers can thus be varied linearly while maintaining the mechanical integrity of the device. The initial strength of such surface erosion polymers tends to be low however, and often such surface erosion polymers are not readily available commercially. Nevertheless, examples of surface erosion polymers that could be used to help vary the drug delivery rate of a device according to the systems and methods of the invention include polyanhydrides such as poly (carboxyphenoxy hexane-sebacic acid), poly (fumaric acid-sebacic acid), poly (carboxyphenoxy hexane-sebacic acid), poly (imide-sebacic acid) (50-50), poly (imide-carboxyphenoxy hexane)(33-67), and polyorthoesters (diketene acetal based polymers).

Bulk erosion polymers, on the other hand, are typically hydrophilic with water labile linkages. Hydrolysis of bulk erosion polymers tends to occur at more uniform rates across the polymer matrix of the device. As a result, bulk erosion polymers release initial bursts of drugs during breakdown of the polymer matrix during absorption. Bulk erosion polymers exhibit superior initial strength and are readily available commercially.

Examples of bulk erosion polymers usable with the drug delivery devices according to the system and methods of the invention include poly (α-hydroxy esters) such as poly (lactic acid), poly (glycolic acid), poly (caprolactone), poly (p-dioxanone), poly (trimethylene carbonate), poly (oxaesters), poly (oxaamides), and their co-polymers and blends. Some commercially readily available bulk erosion polymers and their commonly associated medical applications include poly (dioxanone) [PDS® suture available from Ethicon, Inc., Somerville, N.J.], poly (glycolide) [Dexon® sutures available from United States Surgical Corporation, North Haven, Conn.], poly (lactide)-PLLA [bone repair], poly (lactide/glycolide) [Vicryl® (10/90) and Panacryl® (95/5) sutures available from Ethicon, Inc., Somerville, N.J.], poly (glycolide/caprolactone (75/25) [Monocryl® sutures available from Ethicon, Inc., Somerville, N.J.], and poly (glycolide/trimethylene carbonate) [Maxon® sutures available from United States Surgical Corporation, North Haven, Conn.].

Other bulk erosion polymers are also usable with the drug delivery devices according to the systems and methods of the invention, for example, tyrosine derived poly amino acid [examples: poly (DTH carbonates), poly (arylates), and poly (imino-carbonates)], phosphorous containing polymers [examples: poly (phosphoesters) and poly (phosphazenes)], poly (ethylene glycol) [PEG] based block co-polymers [PEG-PLA, PEG-poly (propylene glycol), PEG-poly (butylene terphthalate)], poly (α-malic acid), poly (ester amide), and polyalkanoates [examples: poly (hydroxybutyrate (HB) and poly (hydroxyvalerate) (HV) co-polymers].

Of course, according to the systems and methods of the invention, the drug delivery devices may be made from combinations of surface and bulk erosion polymers in order to achieve desired physical properties and to control the degradation mechanism and drug release therefrom as a function of time. For example, two or more polymers may be blended in order to achieve desired physical properties, device degradation rate and drug release rate. Alternatively, the drug delivery device can be made from a bulk erosion polymer that is coated with a drug containing a surface erosion polymer. For example, the drug coating can be sufficiently thick that high drug loads can be achieved, and the bulk erosion polymer may be made sufficiently thick that the mechanical properties of the device are maintained even after all of the drug has been delivered and the surface eroded.

While the degradation and drug release factors are considered in choosing the bioabsorable polymers that are to comprise the drug delivery device according to the systems and methods of the invention, maintaining the mechanical integrity and resilience of the device is also a factor to consider. In this regard, shape memory polymers help a device to maintain, or remember, its original shape after deployment of the device in the patient. Shape memory polymers are characterized as phase segregated linear block co-polymers having a hard segment and a soft segment. The hard segment is typically crystalline with a defined melting point, and the soft segment is typically amorphous with a defined glass transition temperature. The transition temperature of the soft segment is substantially less than the transition temperature of the hard segment in shape memory polymers. A shape in the shape memory polymer is memorized in the hard and soft segments of the shape memory polymer by heating and cooling techniques in view of the respective transition temperatures as the artisan should appreciate.

Shape memory polymers can be biostable and bioabsorbable. Bioabsorbable shape memory polymers are relatively new and comprise thermoplastic and thermoset materials. Shape memory thermoset materials may include poly (caprolactone) dimethylacrylates, and shape memory thermoplastic materials may include poly (caprolactone) as the soft segment and poly (glycolide) as the hard segment.

The selection of the bioabsorbable polymeric material used to comprise the drug delivery device according to the invention is determined according to many factors including, for example, the desired absorption times and physical properties of the bioabsorbable materials, and the geometry of the drug delivery device.

In order to provide materials having high ductility and toughness, such as is often required for orthopedic implants, sutures, stents, grafts and other medical applications including drug delivery devices, the bioabsorbable polymeric materials may be modified to form composites or blends thereof. Such composites or blends may be achieved by changing either the chemical structure of the polymer backbone, or by creating composite structures by blending them with different polymers and plasticizers. Plasticizers such as low molecular weight poly(ethylene glycol) and poly(caprolactone), and citrate esters can be used. Any additional materials used to modify the underlying bioabsorbable polymer should preferably be compatible with the main polymer system. The additional materials also tend to depress the glass transition temperature of the bioabsorbable polymer, which renders the underlying polymer more ductile and less stiff.

As an example of producing a composite or blended material for the drug delivery device, blending a very stiff polymer such as poly (lactic acid), poly (glycolide) and poly (lactide-co-glycolide) copolymers with a soft and ductile polymer such as poly (caprolactone) and poly(dioxanone) tends to produce a material with high ductility and high stiffness. An elastomeric co-polymer can also be synthesized from a stiff polymer and a soft polymer in different ratios. For example, poly(glycolide) or poly(lactide) can be copolymerized with poly(caprolactone) or poly(dioxanone) to prepare poly(glycolide-co-caprolactone) or poly(glycolide-co-dioxanone) and poly(lactide-co-caprolactone) or poly(lactide-co-dioxanone) copolymers. These elastomeric copolymers can then be blended with stiff materials such as poly(lactide), poly (glycolide) and poly(lactide-co-glycolide) copolymers to produce a material with high ductility. Alternatively, terpolymers can also be prepared from different monomers to achieve desired properties. Macromers and other cross-linkable polymer systems can be used to achieve the desired properties. Such properties are conducive to a drug delivery stent device according to systems and methods of the invention. Of course, the underlying polymer could also be blended with a stiffer polymer to produce a material having stiffer properties, as might be useful in the case of an orthopedic implant having growth factors or other bio-active agents or drugs delivered therefrom according to the systems and methods of the invention.

The drugs or other bio-active agents delivered by the drug delivery devices according to the systems and methods of the invention may include rapamycin, statins and taxol, or any of the other drugs or bio-active agents otherwise identified herein, for example. The drugs or other agents may reduce different indications such as restenosis, vulnerable plaque, angina and ischemic stroke, for example, particularly where the device is a stent. Growth factors, such as fibro-blasts and vascular endothelial growth factors can also be used in lieu of, or together with, the drugs. Such growth factors may be used for angiogenesis, for example.

In addition to the various drugs identified above, the drugs or other agents incorporated into the device can also include cytostatic and cytotoxic agents, such as, heparin, sirolimus, everolimus, tacrolimus, biolimus, paclitaxel, statins and cladribine. The various drugs or agents can be hydrophobic or hydrophilic as appropriate. In some of the examples set forth below, sirolimus was the drug incorporated into the drug delivery devices.

Other drugs or other bio-active agents usable with the drug delivery devices made according to the systems and methods described herein include: antiproliferative/antimitotic agents including natural products such as vinca alkaloids (i.e., vinblastine, vincristine, and vinorelbine), paclitaxel, epipidopophyllotoxins (i.e., etoposide, teniposide), antibiotics (dactinomycin (actinomycinD) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as G(GP) $11_b$/$111_a$ inhibitors and vitronectin receptor antagonists; antiproliferative/antimitotic alkylating agents such as nitrogen mustards (mechlorethamine, cyclophosphamide and anolgs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminglutethimide; hormones (i.e., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e., aspirin; para-aminphenol derivatives i.e., acetominophen; indole and indene acetic acids (indomethacin, sulindac, and etodalac), heteroaryl acetic acids (tolmetin, diclofenac, and ketorolac), arylpropionic acids (tometin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate (mofetil); angiogenic agents: vascular endothelial growth factor (VEGF), fibroblast growth factor (FGF); angiotensin receptor blockers; nitric oxide donors; anti-sense oligionucleotides and combinations thereof, cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The amount of drugs or other agents incorporated within the drug delivery device according to the systems and methods of the invention can range from 0 to 99% (% weight of the device). The drugs or other agents can be incorporated into the device in different ways. For example, the drugs or other agents can be coated onto the device after the device has been formed, wherein the coating is comprised of bioabsorbable polymers into which the drugs or other agents are incorporated. Alternatively, the drugs or other agents can be incorporated into the matrix of bioabsorbable materials comprising the device. The drugs or agents incorporated into the matrix of bioabsorbable polymers can be in an amount the same as, or different than, the amount of drugs or agents provided in the coating techniques discussed earlier if desired. These various techniques of incorporating drugs or other agents into, or onto, the drug delivery device may also be combined to optimize performance of the device, and to help control the release of the drugs or other agents from the device.

Where the drug or agent is incorporated into the matrix of bioabsorbable polymers comprising the device, for example, the drug or agent will release by diffusion and during degradation of the device. The amount of drug or agent released by diffusion will tend to release for a longer period of time than occurs using coating techniques, and can often more effectively treat local and diffuse lesions or conditions therefore. For regional drug or agent delivery such diffusion release of the drugs or agents is effective as well.

The drug delivery device according to the systems and methods of the invention preferably retains its mechanical integrity during the active drug delivery phase of the device. After drug delivery is achieved, the structure of the device ideally disappears as a result of the bioabsorption of the materials comprising the device. The bioabsorbable materials comprising the drug delivery device are preferably biocompatible with the tissue in which the device is implanted such that tissue interaction with the device is minimized even after the device is deployed within the patient. Minimal inflammation of the tissue in which the device is deployed is likewise preferred even as degradation of the bioabsorbable materials of the device occurs.

Because visualization of the drug delivery device as it is implanted in the patient is helpful to the medical practitioner for locating and orienting the device, and for maximizing the dispersal of the drugs or other agents to an intended site once implanted, radiopaque materials may be added to the device. The radiopaque materials may be added directly to the matrix of bioabsorbable materials comprising the device during processing thereof, resulting in fairly uniform incorporation of the radiopaque materials throughout the device. Alternatively, the radiopaque materials may be added to the device in the form of a layer, a coating, a band or powder at designated portions of the device, depending on the geometry of the device and the process used to form the device.

Ideally, the radiopaque material does not add significant stiffness to the drug delivery device so that the device can readily traverse the anatomy within which it is deployed. The radiopaque material should be biocompatible with the tissue within which the device is deployed. Such biocompatibility minimizes the likelihood of undesirable tissue reactions with the device. Inert noble metals such as gold, platinum, iridium, palladium, and rhodium are well-recognized biocompatible radiopaque materials. Other radiopaque materials include barium sulfate ($BaSO_4$), bismuth subcarbonate ($(BiO)_2CO_3$), bismuth oxide, tungsten, tantalum, and iodine compounds, at least some of which are used in examples described further below. Ideally, the radiopaque materials adhere well to the device such that peeling or delamination of the radiopaque material from the device is minimized, or ideally does not occur.

Where the radiopaque materials are added to the device as metal bands, the metal bands may be crimped at designated sections of the device. Alternatively, designated sections of the device may be coated with a radiopaque metal powder, whereas other portions of the device are free from the metal powder. As the artisan should appreciate, barium is most often used as the metallic element for visualizing the device using these techniques, although tungsten and other fillers are also becoming more prevalent.

Radiopaque coatings on all or portions of the device can also be used to enhance the radiopacity and visualization of the device deployed within the patient. Such coatings sometimes have less negative impact on the physical characteristics (eg., size, weight, stiffness, flexibility) and performance of the device than do other techniques. Coatings can be applied to the device in a variety of processes known in the art such as, for example, chemical vapor deposition (CVD), physical vapor deposition (PVD), electroplating, high-vacuum deposition process, microfusion, spray coating, dip coating, electrostatic coating, or other surface coating or modification techniques.

Alternatively, the bioabsorbable polymer materials used to comprise the drug delivery device according to the invention can include radiopaque additives added directly thereto during processing of the matrix of the bioabsorbable polymer materials to enhance the radiopacity of the device. The radiopaque additives can include inorganic fillers, such as barium sulfate, bismuth subcarbonate, bismuth oxides and/or iodine compounds. The radiopaque additives can instead include metal powders such as tantalum or gold, or metal alloys having gold, platinum, iridium, palladium, rhodium, a combination thereof, or other materials known in the art. The particle size of the radiopaque materials can range from nanometers to microns, and the amount of radiopaque materials can range from 0-99% (wt %).

Because the density of the radiopaque additives is typically very high where the radiopaque materials are distributed throughout the matrix of bioabsorbable materials, dispersion techniques are preferably employed to distribute the radiopaque additives throughout the bioabsorbable materials as desired. Such techniques include high shear mixing, surfactant and lubricant additions, viscosity control, surface modification of the additive, and other particle size, shape and distribution techniques. In this regard, it is noted that the radiopaque materials can be either uniformly distributed throughout the bioabsorbable materials of the device, or can be concentrated in sections of the device so as to appear as markers similar to as described above.

Preferred low temperature processes of forming the drug delivery devices according to the systems and methods of the invention include solution processing and supercritical fluid processing techniques. These processes include solvent extraction, coating, wire-coating, extrusion, co-extrusion, fiber-spinning including electrostatic fiber-spinning, lyophilization and other techniques that incorporate drugs or other bio-active agents that are unstable at high temperatures into the matrix of bioabsorbable polymeric materials that will comprise the drug delivery device. For drugs or agents that are stable at high temperature, different melt processing techniques may instead be used to incorporate the drugs or agents into the matrix of bioabsorbable polymers that comprise the device. Alternatively, the drugs or agents may be sprayed, dipped, or coated onto the device after formation thereof from the bioabsorbable polymers. In either case, the polymer matrix, and drug or agent blend when provided, is then converted into a structure such as fibers, films, discs/rings or tubes, for example, that is thereafter further manipulated into various geometries or configurations as desired.

Different processes can thus provide different structures, geometries or configurations to the bioabsorbable polymer being processed. For example, tubes processed from rigid polymers tend to be very stiff, but can be very flexible when processed via electrostatic processing or lyophilization. In the former case, the tubes are solid, whereas in the latter case, the tubes are porous. Other processes provide additional geometries and structures that may include fibers, microfibers, thin and thick films, discs, foams, microspheres and even more intricate geometries or configurations. Melt or solution spun fibers, films and tubes can be further processed into different designs such as tubular, slide and lock, helical or otherwise by braiding and/or laser cutting. The differences in structures, geometries or configurations provided by the different processes are useful for preparing different drug delivery devices with desired dimensions, strengths, drug delivery and visualization characteristics.

Different processes can likewise alter the morpohological characteristics of the bioabsorbable polymer being processed. For example, when dilute solutions of polymers are stirred rapidly, the polymers tend to exhibit polymer chains that are generally parallel to the overall axis of the structure. On the other hand, when a polymer is sheared and quenched to a thermally stable condition, the polymer chains tend to elongate parallel to the shear direction. Still other morphological changes tend to occur according to other processing techniques. Such changes may include, for example, spherulite to fibril transformation, polymorphic crystal formation change, re-orientation of already formed crystalline lamellae, formation of oriented crystallites, orientation of amorphous polymer chains and/or combinations thereof.

In the case of a drug delivery device comprised of bioabsorbable polymeric materials according to the systems and method of the invention, the device may be formed by solution spinning fibers or solvent cast films or tubes, for example, wherein the polymer fibers, films or tubes are typically formed at ambient conditions. As a result, drugs incorporated therein the bioabsorbable polymeric materials do not degrade as readily. After formation, the fibers, films or tubes are laser cut to a desired geometry or configuration such as in the shape of a stent, for example, including a helical pattern as shown in FIGS. 1 thru 3.

Figure 2:
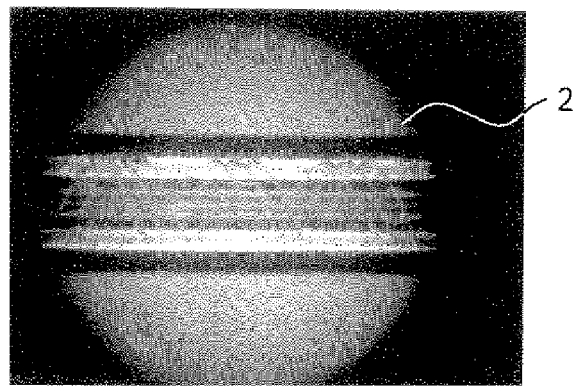
FIG. 2 illustrates a helical open lattice stent according to the systems and methods of the invention.
Figure 3:
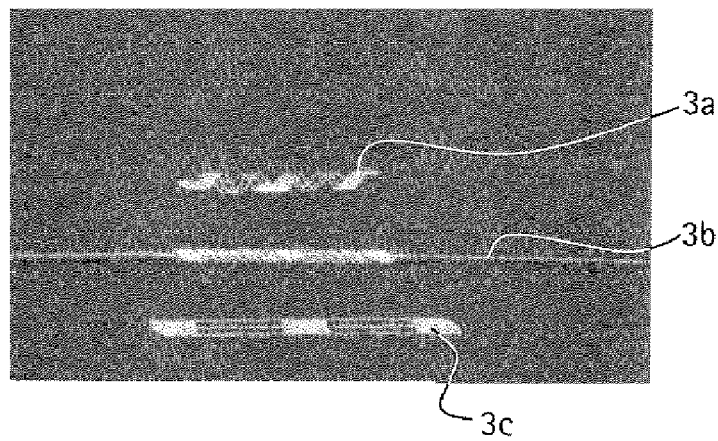
FIG. 3 illustrates a helical stent having a hybrid solid ladder and open lattice design in a deployed state, a balloon mounted state, and in a film cut precursor state according to the systems and methods of the invention.

The helical stent can be a solid ladder pattern 1a as shown in FIG. 1, or can be more of an open lattice pattern 2 as shown in FIG. 2. Hybrids 3a of a solid ladder pattern with an open lattice pattern can also comprise the stent, as in FIG. 3, if desired.

Figure 4A:
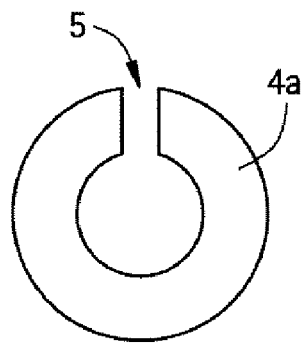
FIGS. 4a-4c illustrate various embodiments of a ring, or wrap, according to the systems and methods of the invention.
Figure 4B:
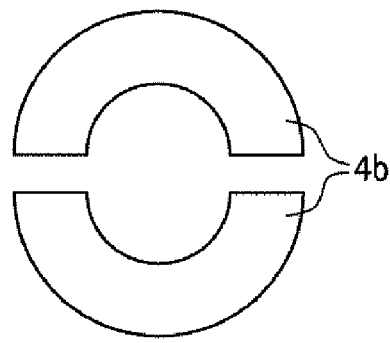
Figure 4C:
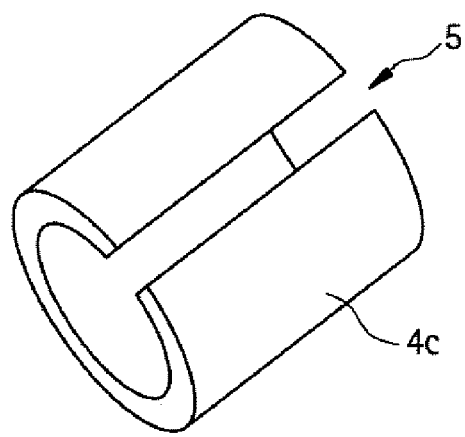

As discussed in greater detail further below, FIG. 1 illustrates the solid ladder stent 1a in a deployed state, in a balloon mounted state 1b, and in a precursor film state 1c from which the stent is made. FIG. 3 likewise illustrates the hybrid stent 3a in a deployed state 3a, in a balloon mounted state 3b, and in a film precursor state 3c. Although not shown, the open lattice stent 2 is understood to have similar deployed, balloon mounted and precursor film states according to the systems and methods of the invention. In either case, the stent is comprised of bioabsorbable polymeric materials into, or onto, which drugs or other bio-active agents and/or radiopaque additives are combined during the processing thereof, as described in more detail in the Examples set forth below. After formation of the bioabsorbable polymeric materials into a tube, film, fiber or other structure with the drugs, agents and/or radiopaque materials incorporated therein or thereon, the tubes, films, fibers or other structures can be laser cut, braided or otherwise worked into the helical stent or other geometry to form the drug delivery device as desired. Of course, the device may instead be worked into a non-stent device comprised of a ring, or wrap, FIGS. 4a-4c, for example, wherein the drugs or other agents and radiopaque markers are incorporated into or onto the bioabsorbable materials forming the device. FIG. 4a shows a ring 4a with a slit (s) enabling the ring 4a to be fitted over a vessel, for example, whereas FIG. 4b shows a pair of semicircular wraps 4b that may be sutured together around a vessel, and FIG. 4c shows a cylinder 4c with a slit (s) enabling the cylinder 4c to be fitted over a vessel.

In the case of helical shaped stents comprised of bioabsorbable polymeric materials and drugs or other agents, and/or radiopaque materials as desired, a preferred process of making such stents is solvent casting. For example, the bioabsorbable polymeric materials and additives are solvent cast into a film, cut into strips of desired lengths, laser cut into the helical coil or other design, and mounted and wound onto a heated mandrel to provide a desired interior diameter. The strips can be converted to lower profiles, i.e., having smaller interior diameters, by winding them on a mandrel with a smaller outer diameter. The wound strip is then mounted onto a balloon catheter and heat nested in a nesting tube to attach the wound strip to the balloon (FIGS. 1b and 3b). During balloon inflation, the wound strip detaches from the balloon and expands to form a deployed stent as shown in FIGS. 1a and 3a. The final size of the deployed stent depends on several variables such as interior diameter of the wound strip, interior diameter of the nesting tube, balloon length and expanded outer diameter, and stent material. The radial strength of helical stents made in this manner varies depending on the design (solid ladder, open lattice, or hybrid), wall thickness of the stents, and materials used to comprise the stents. Stiffer polymers such as PLLA and PLGA tend to have the highest radial strength, whereas elastomeric polymers such as PCL/PGA (35/65) tend to have lower radial strength characteristics. The stents can be formed with different materials, as described above, in a manner as described further in Examples set forth below, and can be delivered percutaneously using conventional balloon and self expanding delivery systems. The absorption profile of the stent can be tailored to clinical needs such that drug delivery can occur locally or regionally over designated time periods.

Figure 5A:
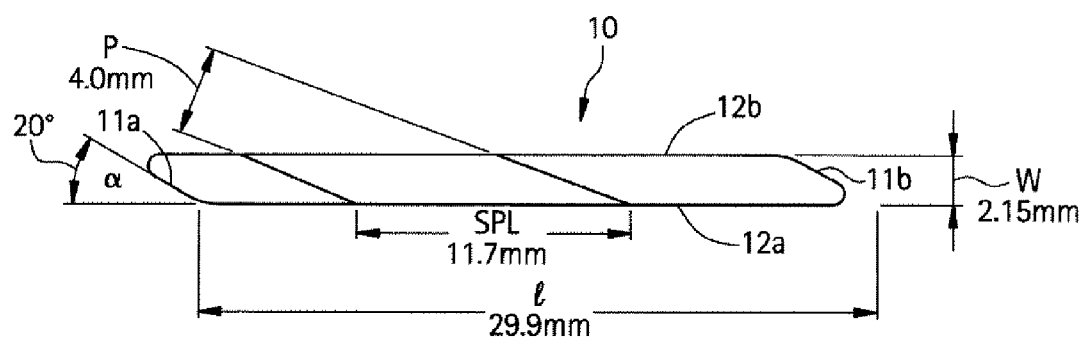
FIG. 5a illustrates a cut film strip having an exemplary dimensional scheme for a solid ladder stent according to the systems and methods of the invention.

FIG. 5a illustrates a film strip 10 from which a solid ladder stent, such as stent 1a of FIG. 1, is made. The film strip 10 is cut from film prepared by solvent cast film methods, for example, or by other methods as described herein. The dimensions shown in FIG. 5a are exemplary only and are understood to be alterable to suit various medical needs.

Figure 5B:
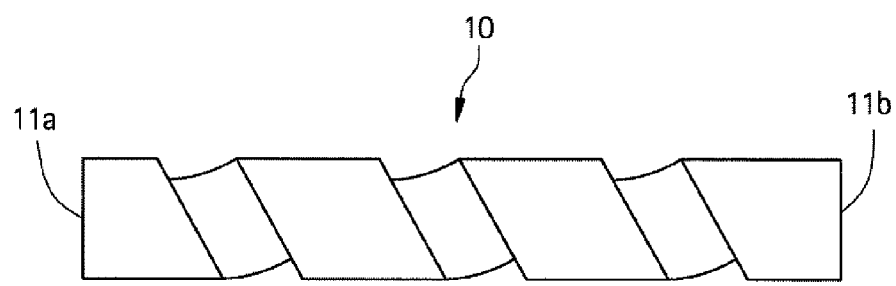
FIG. 5b illustrates a solid ladder stent in a deployed state with squared ends.

In FIG. 5a, the film strip 10 has been cut into approximately 2 mm wide (w) strips of approximately 30 mm in length (l). The film strip 10 is generally comprised of a first pair of opposed sides 12a and 12b, and a second pair of opposed sides 11a and 11b, wherein opposed sides 12a and 12b are longer than opposed sides 11a and 11b. The sides 11a and 11b are cut at angles ($\alpha$) approximately 10-30 degrees, and preferably 20 degrees, relative to a respective side 12a and 12b. The helical axis pitch (P) is approximately 4.0 mm in FIG. 5, and the helical screw pitch length (SPL) is approximately 12 mm. In the case of a solid ladder stent fabricated from the strip 10 of FIG. 5a, alternating struts are not provided in the film strip 10, so as to form the solid portions of the solid ladder stent 1a, for example. In practice, the film strips 10 are coiled about a heated mandrel, shaped and cooled into the desired helical structure as shown in FIG. 1a, for example. Alternatively, and preferably, the film strip 10 is coiled about a mandrel in the presence of heat, shaped and cooled into the helical structure shown in FIG. 5b, wherein sides 11a and 11b are squared ends that are blunter than those shown in the deployed stent 1a shown in FIG. 1. The squared ends of sides 11a and 11b result from the angle $\alpha$ as described above. For example, the sides 11a and 11b in FIG. 5b do not flare out as much as those ends shown in FIG. 1a.

The interior diameter of the stent is determined by the outer diameter of the mandrel on which the film strip 10 is coiled. Cutting the sides 11a and 11b of the stent at angles $\alpha$ provides improved fluid flow through the lumen of the stent, whereby an angle $\alpha$ of 20 degrees provides even more uniform and less turbulent fluid flow through the stent. Such contributes to improved endothelialization and tissue healing with respect to the vessel, or other passageway, in which the stent is implanted. Of course, the artisan will appreciate that the film strips can be cut into other shapes and geometries as desired.

Figure 6A:
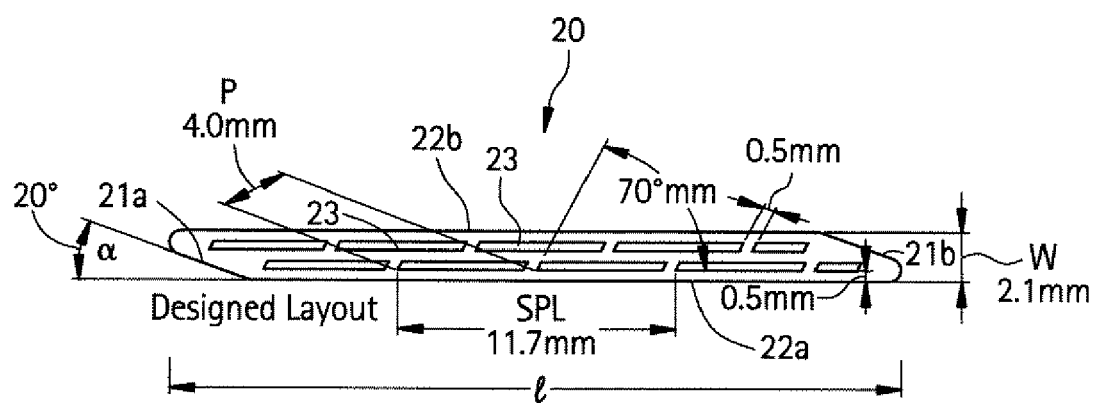
FIG. 6a illustrates a cut film strip having an exemplary dimensional scheme for an open lattice stent according to the systems and methods of the invention.

FIG. 6a illustrates a film strip 20 from which an open lattice stent, such as stent 2 of FIG. 2 is made, the film strip 20 having been cut from film prepared by solvent cast film methods, or other methods as described herein. The dimensions shown in FIG. 6a are exemplary only and are understood to be alterable to suit various medical needs. In FIG. 6a, the film has been cut into approximately 2 mm wide (w) strips of approximately 30 mm in length (l), and includes pairs of opposed sides 22a and 22b, and 21a and 21b, similar to as described with respect to FIG. 5a. The opposed sides 21a and 21b are cut at angles α of approximately 10-30 degrees, and preferably 20 degrees, relative to a respective side 22a and 22b, and the helical axis pitch (P) is approximately 4.0 mm. The helical screw pitch length (SPL) is approximately 12 mm. Approximately four alternating struts 23 are included per SPL cycle in order to form the open lattice helical stent as in FIG. 2.

Figure 6B:
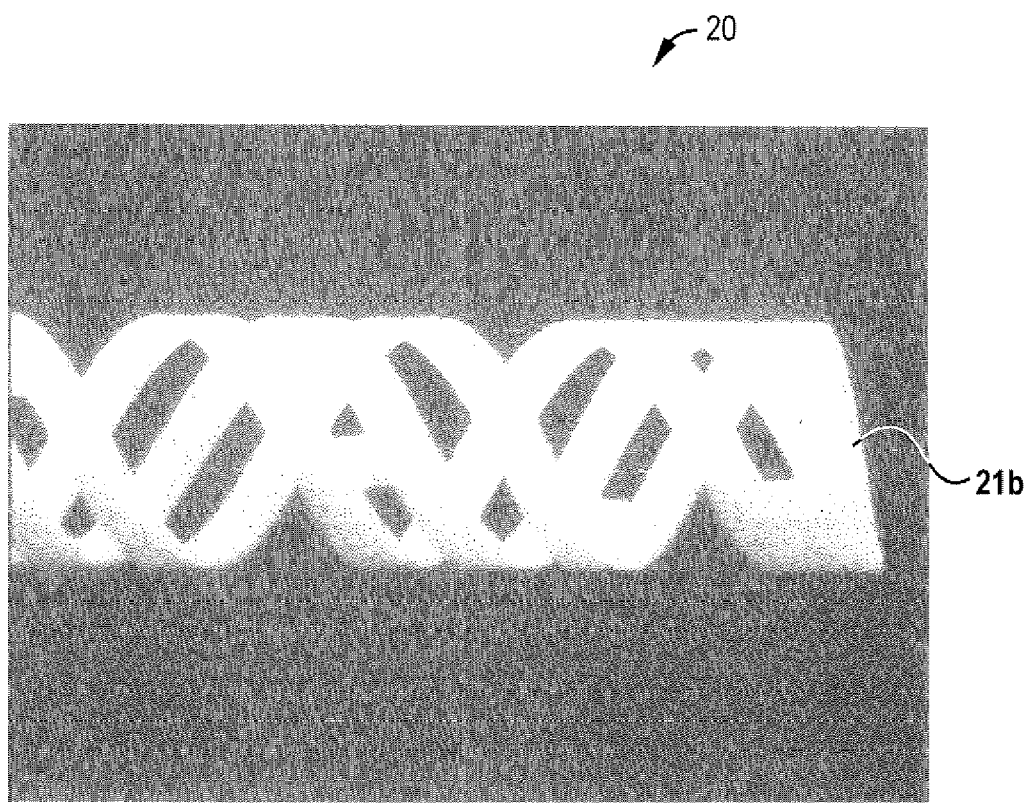
FIG. 6b illustrates an open lattice stent in a deployed state with squared ends.
Figure 9:
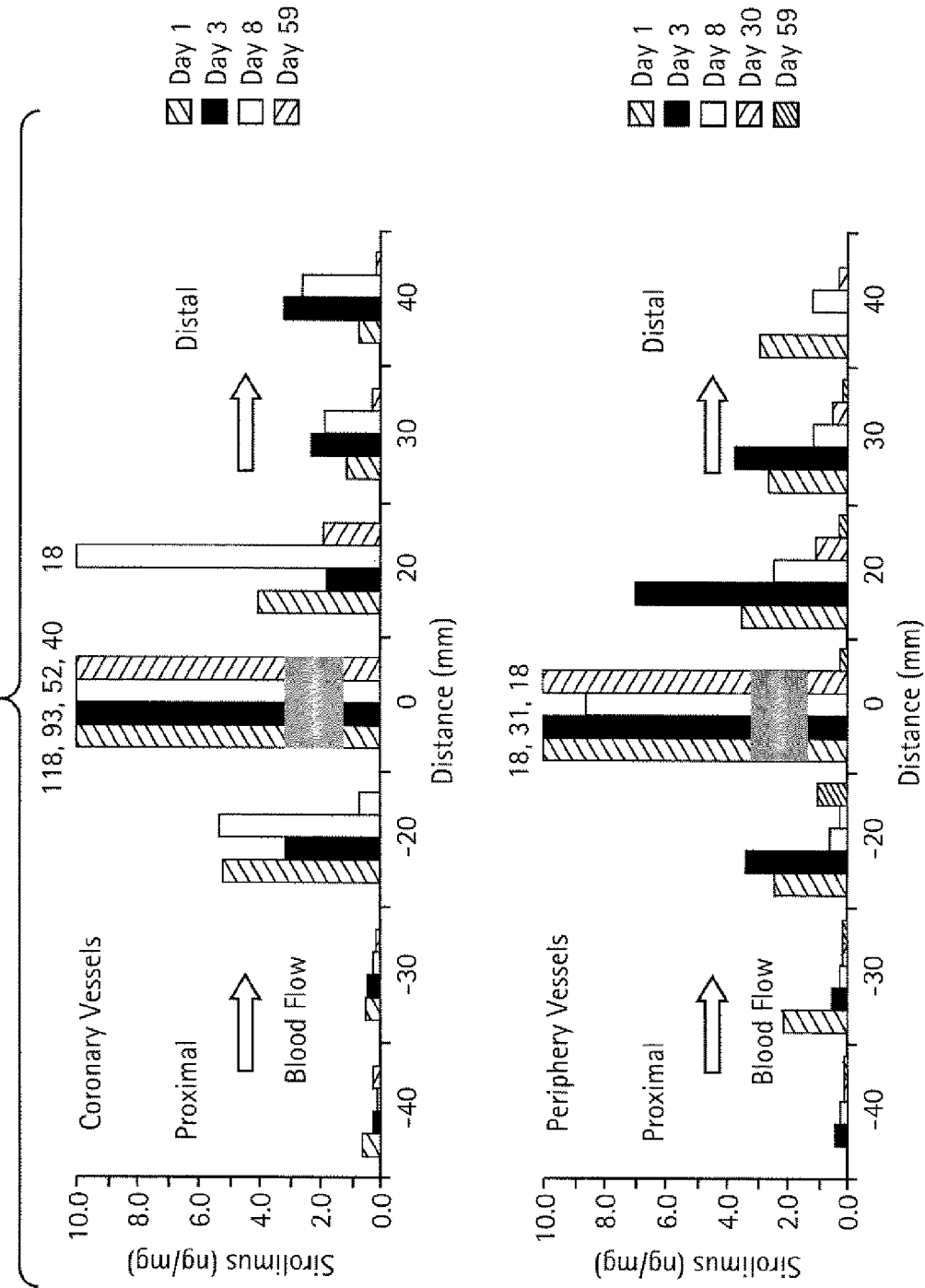
FIG. 9 illustrates a graph showing drug uptake in vessel tissue according to the systems and methods of the invention.
Figure 10:
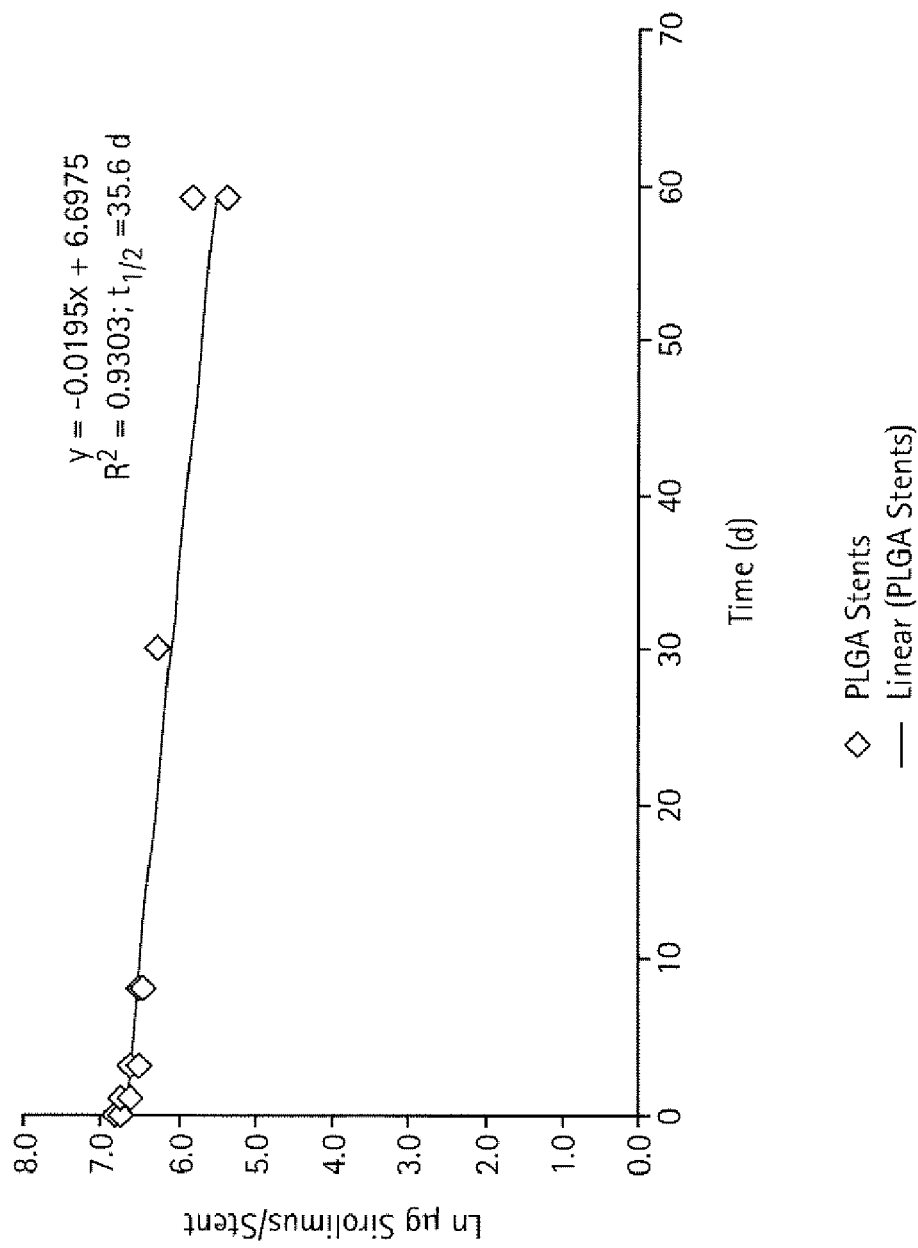
FIG. 10 illustrates a graph showing drug elution pharmacokinetics according to the systems and methods of the invention.

Referring still to FIG. 6a, the interior diameter of the stent is determined by the outer diameter of the mandrel on which the film strip 20 is coiled. Cutting the sides 21a and 21b of the stent at angles α provides improved fluid flow through the lumen of the stent, whereby an angle α of 20 degrees provides even more uniform and less turbulent fluid flow through the stent. This is mainly because, referring to FIG. 6b, the stents with sides 21a and 21b at such 20 degree angles provide blunt, or squared, ends (sides 21a, 21b) as shown in FIG. 6b. The bluntness of sides 21a, 21b in FIG. 6b (only side 21b shown in FIG. 6b) differs from the generally flared out ends of the deployed stent 2 of FIG. 2, for example, or more generally any of the deployed stents depicted in FIGS. 1-3. Such contributes to improved endothelialization and tissue healing with respect to the vessel, or other passageway, in which the stent is emplaced. The stent as shown in FIGS. 6a-6b also has been found in animal studies to provide improved regional drug diffusion and tissue uptake of the drug even beyond proximal and distal ends of the stent when emplaced in the animal. FIGS. 9 and 10 are graphs illustrating such drug diffusion and pharmacokinetics along these lines. Of course, the artisan will appreciate that the film strips can be cut into other shapes and geometries as desired.

Although not shown, hybrid stents such as those shown in FIG. 3 are similarly made using combinations of the methods, dimensions and geometries of FIGS. 5a and 6b, as should be readily evident to the artisan.

Examples I-III, set forth below, describe the production of solvent cast films to comprise a drug delivery device according to the invention, wherein the devices are comprised of bioabsorbable polymeric materials comprised of polylactide/polyglycolide copolymers such as PLA/PGA (95/5 and 85/15), and blends thereof. Blends were prepared to make stiff polymers more ductile and flexible in order to prepare stents that require more strain values. Different solvents were used to prepare the films such as chloroform, dioxane, and binary solvent mixtures such as dioxane/acetone and dioxane/ethyl acetate. Different radiopaque agents were used from 10 to 40% (by weight) from materials including barium sulfate, bismuth subcarbonate, and bismuth oxide. Sirolimus was used as the drug in these films from 5 to 30% (by weight).

Figure 7:
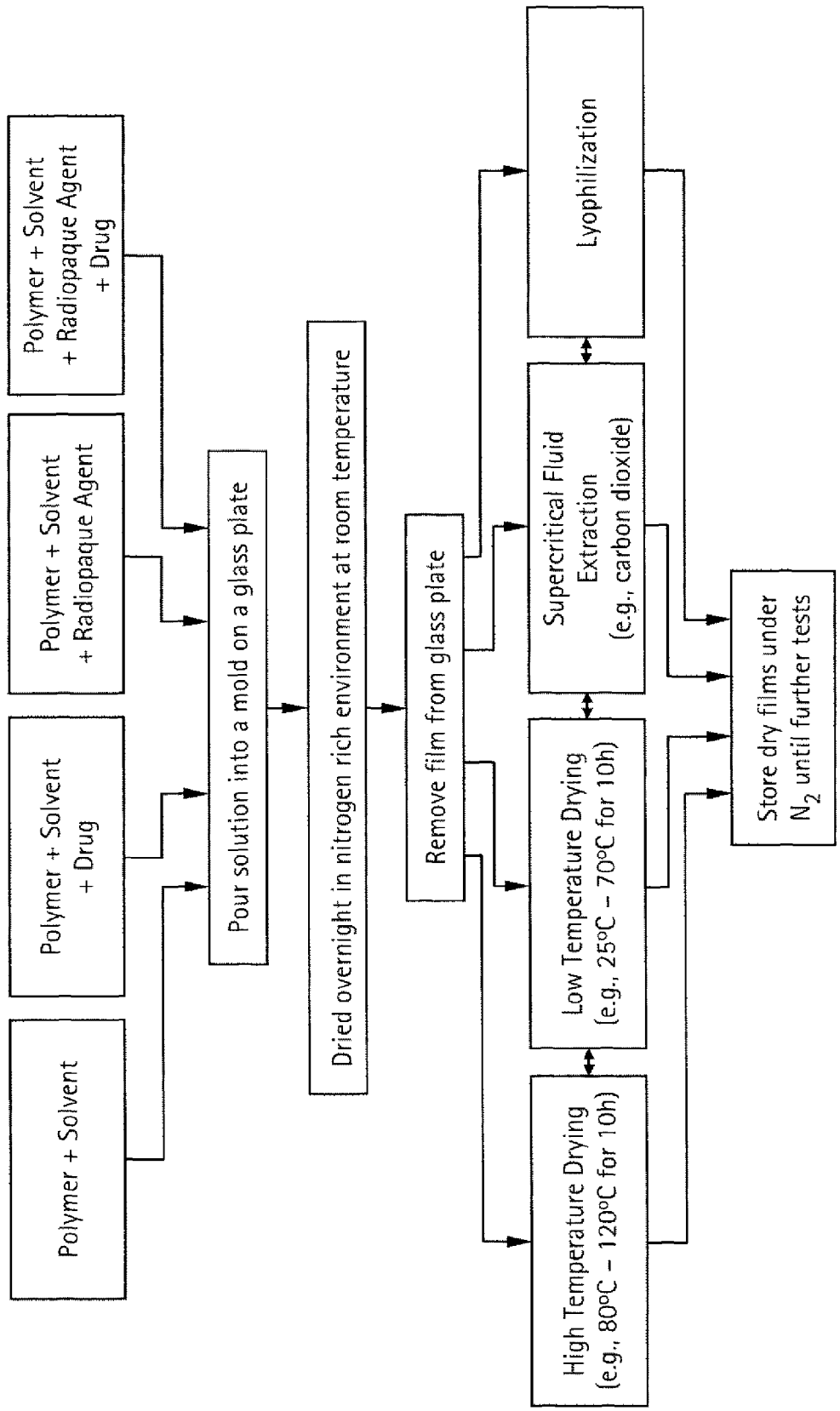
FIG. 7 illustrates a flow diagram of a film fabrication process according to the systems and methods of the invention.

FIG. 7 shows a typical film fabrication process. Polymer resins are added to a given solvent and tumbled with or without heat until the polymer dissolves completely in the solvent to provide a homogenous solution. Polymer formulations can be prepared using these solutions that may include radiopaque agents, drug or combinations thereof. These formulations are tumbled and mixed properly in order to prepare uniform dispersions. These formulations can be converted to films by pouring them in a mold on to a glass plate and allowing the solvent to evaporate overnight in a nitrogen rich environment at room temperature. The film may be removed from the glass plate and the solvent can be further removed under conditions including high temperature oven drying (e.g., 110° C. for 10 hours), low temperature oven drying (e.g., 25° C. to 60° C. for 6 hours), low temperature carbon dioxide extraction (e.g., 40° C. at 60 to 80 bar pressure for 20 to 60 minutes), lyophilization and combinations thereof. Low temperature drying is used to preserve drug content in the films. The drying conditions will also determine the morphology (amorphous or crystalline) of the films. After drying, the films can then be stored in an inert environment (nitrogen box) until further testing and prototyping.

Example I

Polymer with Drug/Agent

Preparation of PLA/PGA 95/5 Films with Sirolimus from Chloroform
  PLA/PGA 95/5 resin was obtained from Purac Inc., with an intrinsic viscosity of about 2.2.
  A summary of a film making protocol is given below:
    Prepare PLA/PGA stock solution at 4.3% by weight by dissolving PLA/PGA in chloroform and tumbling the solution overnight at room temperature.
    Add sirolimus in desired amounts of 0 to 30% to the stock solution.
    Pour a predetermined mass of the PLA/PGA and drug into a mold positioned in the center of a glass plate (12" by 12").
    Cover the mold to reduce the rate of chloroform evaporation.
    Slowly dry the films overnight at room temperature in a nitrogen rich environment.
    Release the films from the glass plates.
    Dry further to remove residual solvent under different conditions as described above.
    Other post treatment of the films including annealing and orientation at different temperatures can be performed.
    Cut the film into strips as desired and store until needed.
    Thereafter, the film strips may be laser cut into desired shapes and geometries, including the helical solid ladder, open lattice or hybrids thereof described above.
  Prior to cutting the films into 2 mm wide strips, for example, the film uniformity was verified by measuring film thickness in five regions, i.e, at each corner and at the center of each film. In general, film thickness averaged 150 microns among all samples with a maximum thickness of 220 microns in the films containing 30% sirolimus.

Example II

Polymer with Drugs/Agents and Radiopaque Material

Preparation of PLA/PGA (95/5) Films with Sirolimus and Radiopaque Agents
  PLA/PGA 95/5 and 85/15 resins were obtained from Purac Inc., with an intrinsic viscosity of about 2.2 and 2.3, respectively. Barium sulfate of different particle size (1 and 0.1 microns) was obtained from Reade Advanced Material and Sachtleben Corporation. Bismuth subcarbonate and bismuth oxide were obtained from Spectrum and Nanophase Technologies Corporation, respectively.
  In general, the radiopaque agents are added after the preparation of the PLA/PGA stock solution prepared above as in Example I. The formation of the films then generally continues as otherwise set forth in Example I except as otherwise detailed herein with respect to the various radiopaque agents. The radiopaque agents may be barium sulfate or bismuth subcarbonate. The radiopaque agents are added to the PLA/PGA solution by sonication, by high speed mixing, or by tumbling. Sonication was found to more effectively disperse barium sulfate in the stock solution than it did bismuth subcarbonate. The PLA/PGA stock solution was 12% (by weight). Preparation of films containing specific radiopaque agents in varying concentrations are detailed further below.

Super-critical fluids could also be used to remove any residual solvent.

a. Preparation of PLA/PGA (95/5) Films Containing Barium Sulfate (Blanc Fixe XR-HN, Particle Size 1 Micron)

Solutions containing 10%, 20% and 30% by weight barium sulfate (based on total solids) as the radiopaque agent and a fixed level of sirolimus (15% w/w, based on drug and polymer) were prepared in the following manner:

Prepare PLA/PGA stock solution at 15.0% by weight.
Dissolve target mass of PLA/PGA in chloroform and tumble the solution overnight at room temperature
Weigh target mass of barium sulfate in an amber bottle.
Weigh target mass of chloroform into the same amber bottle.
Sonicate the barium sulfate in chloroform for 20 minutes.
Weigh target mass of sirolimus into a pre-cleaned amber bottle.
Weigh PLA/PGA stock solution into sirolimus containing bottle.
Add barium sulfate dispersion to the PLA/PGA stock solution.
Purge any air gap with nitrogen gas and seal the bottle.
Tumble complete formulation overnight.
Filter through stainless steel mesh (25 micron hole size) to remove larger particles.
Weigh desired mass of solution (about 90 g is required to cast a film) into three separate jars.
Let stand at room temperature for a minimum of 1 hour to remove bubbles. Gently swirl for about 3 minutes.
Pour the solution into the mold and re-weigh the jar after the transfer.
The difference in mass represents the mass of coating solution used to prepare the film.
Release the film from glass plate and dry the film as described above.
Place the dried films in a box purged with nitrogen for storage.
Thereafter the films can be laser cut or otherwise worked into a desired geometry and stored until needed.

A summary of the weights used to prepare the three coatings solutions including various concentrations of barium sulfate (XR-HN), based on a target mass of about 200 g, is provided immediately below.

| Compositions of Solutions Used to Prepare Films | | | |
|---|---|---|---|
| | Target Loading (% w/w) of Barium Sulfate (Blanc Fixe XR-HN) | | |
| Reagent | 10% | 20% | 30% |
| Barium sulfate (g) | 1.12 | 2.51 | 4.28 |
| Chloroform (g) | 143.98 | 142.80 | 140.23 |
| Sirolimus (g) | 1.5127 | 1.5165 | 1.5163 |
| PLA/PGA, (14.99% w/w) | 56.60 | 57.01 | 56.71 |
| Total mass (g) | 203.21 | 203.84 | 202.74 |

| Compositions of Solutions Used to Prepare Films | | | |
|---|---|---|---|
| | Target Loading (% w/w) of Barium Sulfate (Blanc Fixe XR-HN) | | |
| Reagent | 10% | 20% | 30% |
| Actual BaSO$_4$ content (%) | 10.1 | 20.0 | 29.9 |
| Actual Sirolimus content (%) | 15.14 | 15.07 | 15.14 |

Different grades and particle size (e.g., 0.1 micron) of barium sulfate can be used to prepare similar formulations.

b. Preparation of PLA/PGA Films Containing Bismuth Subcarbonate

Solutions containing 10%, 20% and 30% by weight bismuth subcarbonate (particle size of about 9 microns) and a fixed amount of sirolimus (15% w/w) were prepared using a slightly modified procedure than as described above for other radiopaque agent films. Films containing dispersed bismuth subcarbonate contained a greater fraction of larger particles than films loaded with barium sulfate. As a result, the salt containing PLA/PGA solution was tumbled for a longer period of time (3 days) to allow the shearing action of the polymer to assist in breaking up agglomerated salt particles.

After 3 days of tumbling, sirolimus drug was added directly into the amber bottles containing the salt and polymer dissolved in chloroform. The complete procedure to prepare the formulations and films were similar to that described above.

c. Preparation of PLA/PGA (85/15) Films Containing Bismuth Oxide as Radiopaque Agents from Dioxane:

Bismuth oxide was evaluated in powder form as well as in pre-dispersed form in dioxane. The target compositions are shown below:

PLA-PGA (85:15) containing 20% bismuth oxide (NANOARC™) cast from stabilized dioxane
PLA-PGA (85:15) containing 20% bismuth oxide predispersed (NANOTEK ®) in dioxane
PLA-PGA (85:15) containing 30% bismuth oxide cast from stabilized dioxane The bismuth oxide predispersion in dioxane (bismuth oxide in 1,4-dioxane at 19.8 wt %) contained dispersing agents at 1-3% by weight. In film form, these dispersants contribute significantly to the overall composition of the film.

The steps used to formulate the three casting dispersions are described below:
A parent PLA-PGA (85:15) solution in dioxane was prepared at 8.50% by weight.
A parent bismuth oxide dispersion was prepared. This dispersion was used to formulate dispersions containing 20% and 30% bismuth oxide, on a total solids basis.
Part of the parent dispersion was reduced with dioxane to produce the dispersion with 30% bismuth oxide, on a total solids basis.
Another portion of the parent dispersion was reduced with dioxane and the parent polymer solution (8.5% w/w) to achieve 20% bismuth oxide.
A known mass of the bismuth oxide dispersion (19.8% w/w) was added to a PLA-PGA solution at 6.50% by weight to prepare the dispersion containing 20% bismuth oxide.
Of course, drugs or other bioactive may be incorporated herein as in other described examples.

Preparation of Parent Casting Dispersion

A 1" tubular mixing assembly was used for preparing dispersions. The steps used to make up the dispersions are summarized below:

Weigh and add the target mass of stabilized dioxane into a clear wide mouth jar (500 mL capacity).

Weigh and add a portion of the 8.5% w/w PLA-PGA solution, (about 12% of target mass to be added) into the same jar.

Position the mixing head just above the base of the jar and screw the cap tightly. Mix at 10,000 rpm. The polymer helps disperse the bismuth oxide and minimizes splatter on the walls.

Slowly add the target mass of bismuth oxide into the jar under high agitation (10,000 rpm) using a funnel over a period of 3 to 5 minutes. Disperse the mixture at 10,000 rpm for 7 minutes.

Pour the remainder of the polymer solution (8.5% w/w) into the jar under agitation and mix for an additional 5 minutes.

Filter the dispersion through a 25 micron pore size mesh using a 50 mL glass syringe fitted with a stainless steel filtration housing.

Films were prepared from these three dispersions by pouring them in to the molds as described earlier. In this case, the films were dried at 110° C. for 12 hours.

In general, the surface of the films is relatively smooth with no noticeable agglomerates or surface imperfections. The film prepared from bismuth oxide predispersed in dioxane appears to be the smoothest of the three film types. The average film thickness was about 120 microns.

Similar films were prepared from other contrast agents such as iodine compounds, tungsten, and tantalum.

d. Preparation of PLA/PGA (95/5 and 85/15) Films Containing Barium Sulfate as Radiopaque Agents from Dioxane and Chloroform:

PLA-PGA Films from Dioxane:

PLA-PGA casting solutions were prepared in dioxane. Films were prepared by pouring the solution into a clear wide-mouth jar and let the casting solution stand at room temperature for about 30 minutes to allow bubbles to escape. Gently swirl the dispersion for about 2 minutes and pour into the mold. Pour casting solutions with or without barium sulfate directly into the mold. Place a cover over the mold and purge the atmosphere above the film with nitrogen.

The films were dried at room temperature for 18 hours followed by 45° C. drying for 18 hours. The films were dried at 110° C. for 10 hours. The dried films had 20% barium sulfate by weight.

The three most uniform strips from each film were selected for mechanical testing. The measurements were performed in accordance with the test method described in ASTM D 882-02, "Tensile Properties of Thin Plastic Sheeting" using an Instron tensile tester at 23±2° C. and 50±5% R.H.

A summary of the mechanical properties of the PLA/PGA films reported as an average over three test specimens is given in Table I below. Pure PLA-PGA films as well as films containing barium sulfate were tested. Of course, drugs or bioactive may be added as in earlier described examples. In general, films prepared from the two grades (95:5 and 85:15) of PLA-PGA displayed similar physical properties.

The pure PLA-PGA films had elongation values in the 2% to 4% range, for both grades of PLA-PGA. The addition of barium sulfate lowers elongation values by about 10% to 15%. The addition of barium sulfate did not change the general appearance of the stress/strain curves.

TABLE I

Tensile Properties of PLA-PGA Films Cast from Dioxane

| Sample | Stress at Yield (MPa) | Strain at Yield (%) | Modulus (MPa) | Stress at Break (MPa) | Strain at Break (%) | Toughness (MPa) |
|---|---|---|---|---|---|---|
| PLA-PGA (85:15) Series | | | | | | |
| Pure 85:15 | 68.8 | 3.03 | 4092 | 65.12 | 4.55 | 9.97 |
| 85:15 with BaSO$_4$ | 62.9 | 2.74 | 4380 | 58.10 | 3.79 | 11.45 |
| PLA-PGA (95:5) Series | | | | | | |
| Pure 95:5 | 70.9 | 3.79 | 2905 | 66.5 | 4.42 | 20.5 |
| 95:5 with BaSO$_4$ | 57.7 | 3.04 | 3766 | 50.8 | 4.08 | 18.3 |

*Strain at yield and strain at break as well as the modulus were calculated based on grip separation and not extensometer values.

The modulus of the films was calculated using the segment modulus between 0.5% and 1.5% strain by grip separation. The specific limits selected to determine the modulus vary somewhat from film to film.

Other films were made from various PLA-PGA polymer blends in the presence of a chloroform solvent. These solutions and films were otherwise prepared the same way as described above using the solvent dioxane. Again, drugs or other bioactive agents may be added as in earlier described examples.

A summary of the mechanical properties of the PLA-PGA/chloroform films reported as an average over at least three test specimens is given in Table II below. Pure PLA-PGA films as well as films containing barium sulfate were tested.

TABLE II

Tensile Properties of PLA-PGA Films Cast from Chloroform

| Sample I.D. | Stress at Yield (MPa) | Strain at Yield (%) | Modulus (Mpa) | Stress at Break (MPa) | Strain at Break (%) | Toughness (MPa) |
|---|---|---|---|---|---|---|
| PLA-PGA (85:15) Series | | | | | | |
| Pure 85:15 | 65.4 | 3.0 | 4119 | 62.3 | 3.5 | 9.0 |
| 85:15 with BaSO$_4$ | 60.4 | 3.1 | 2843 | 55.8 | 3.9 | 12.1 |
| PLA-PGA (95:5) Series | | | | | | |
| Pure 95:5 | 74.1 | 3.4 | 3690 | 63.7 | 9.8 | 8.8 |
| 95:5 with BaSO$_4$ | 66.1 | 3.8 | 3311 | 58.7 | 8.2 | 13.4 |

*Strain at yield and strain at break as well as the modulus were calculated based on grip separation and not extensometer values.

In general, films prepared from the two grades (95:5 and 85:15) of PLA-PGA displayed similar physical properties:

Example III

Preparation of Polymer Films with Barium Sulfate Using Solvent Binary Mixtures

The materials used throughout Example III are summarized below. PLA/PGA 85/15 and 95/5 were obtained from Purac Inc., with an intrinsic viscosity of about 2.2 and 2.3, respectively. Barium sulfate was obtained from Reade Advanced Material.

Preparation of Casting Solutions

Pure PLA-PGA Casting Solutions

Four pure polymer casting solutions were prepared, two using the 95:5 grade PLA/PGA and two using the 85:15 grade PLA-PGA as shown below:

PLA-PGA (95:5) dissolved in a 50:50 w/w % mixture of dioxane/acetone and dioxane/ethyl acetate.

PLA-PGA (85:15) dissolved in a 25:75 w/w % mixture of dioxane/acetone and dioxane/ethyl acetate.

The table below summarizes the weights used to prepare the casting solutions.

| Composition of Barium Sulfate-Containing Casting Dispersions | | |
|---|---|---|
| Ingredient | % by Weight of Different Ingredients | |
| Barium sulfate | 1.39 | 1.41 |
| PLA-PGA (85:15) | 5.03 | 5.01 |
| Dioxane:acetone (25:75 w/w %) | 93.58 | — |
| Dioxane:ethyl acetate (25:75 w/w %) | — | 93.58 |
| Target mass (g) of casting solution poured into rectangular (5 × 7 in²) mold | 66 | 66 |
| Barium sulfate | 1.16 | 1.14 |
| PLA-PGA (95:5) | 4.04 | 4.04 |
| Dioxane:acetone (50:50 w/w %) | 94.80 | — |
| Dioxane:ethyl acetate (50:50 w/w %) | — | 94.82 |
| Target mass (g) of casting solution poured into rectangular (5 × 7 in²) mold | 83 | 82 |

Films were prepared from these dispersions as described earlier and were dried at 110° C. for 12 hours to remove residual solvents.

Drugs or other bioactive agents may be added as in earlier described examples.

A summary of the mechanical properties of the PLA-PGA film blends is reported as an average of at least three test specimens in the Table III below.

In general, films cast from PLA-PGA (85:15) were of better quality than films prepared from the 95:5 grade of the polymer regardless of the solvent mixture.

In general, films prepared from the different solvent mixtures displayed similar physical properties.

Films prepared using the 85:15 grade of PLA-PGA cast from 25:75 mixtures of dioxane:acetone or dioxane:ethyl acetate displayed elongation values of 3.5%, with good agreement between specimens (standard deviations of less than 6%). The solvent mixture used to dissolve the polymer had little, if any, influence on elongation values. The addition of barium sulfate also had no influence on elongation values.

Films prepared using the (95:5) grade of PLA-PGA cast from 50:50 mixtures of dioxane:acetone or dioxane: ethyl acetate displayed elongation values of 2.7%, with better than expected agreement between films specimens (standard deviations of less than 10%).

Stress at yield values changed very little for these films. The values ranged from 53 to 58 MPa for the 95:5 grade of PLA-PGA and remained essentially unchanged (65 MPa) for the 85:15 of the copolymer. These values were very similar to the stress at break values.

Strain at yield values also changed very little ranging from 2.6 to 3.7% and from 3.2 to 3.5% for the 95:5 and 85:15 grades of PLA-PGA, respectively.

Modulus values did not follow any trend with solvent mixture or addition of barium sulfate. Values ranged from 3423 to 5870 MPa and from 4000 to 5294 MPa for the 95:5 and 85:15 grades of PLA-PGA, respectively. A similar trend was observed for the 95:5 grade of polymer with stress at yield values dropping from 74 to 58 MPa and modulus values from 3690 to 2938 MPa.

TABLE III

Tensile Properties of PLA-PGA Films Cast from Binary Solvent Mixtures

| Sample I.D. | Stress at Yield (MPa) | Strain at Yield (%) | Modulus (MPa) | Stress at Break (MPa) | Strain at Break (%) | Toughness (MPa) |
|---|---|---|---|---|---|---|
| PLA-PGA (95:5) in 50:50 mixtures of dioxane (D) with acetone (A) or ethyl acetate (EA) | | | | | | |
| Pure 95:5 in D:A | 53.0 | 2.6 | 3676 | 53.0 | 2.6 | 3.9 |
| Pure 95:5 in D:EA | 56.3 | 2.8 | 4430 | 56.2 | 2.8 | 4.8 |
| With BaSO₄ in D:A | 57.5 | 3.4 | 5870 | 56.4 | 3.7 | 4.9 |
| With BaSO₄ in D:EA | 57.6 | 3.7 | 3423 | 57.0 | 3.9 | 7.7 |
| PLA-PGA (85:15) in 25:75 mixtures of dioxane (D) with acetone (A) or ethyl acetate (EA) | | | | | | |
| Pure 85:15 in D:A | 64.6 | 3.5 | 3998 | 64.2 | 3.6 | 5.9 |
| Pure BaSO₄ D:EA | 64.2 | 3.3 | 4142 | 63.5 | 3.5 | 7.0 |
| With BaSO₄ in D:A | 66.2 | 3.2 | 5226 | 63.9 | 3.4 | 6.0 |
| With BaSO₄ in D:EA | 65.2 | 3.2 | 5294 | 63.1 | 3.5 | 9.1 |

*Strain at yield and strain at break as well as the modulus were calculated based on grip separation and not extensometer values.

The modulus of the films was calculated using the segment modulus between 0.5% and 1.5% strain by grip separation. The specific limits selected to determine the modulus varied somewhat from film to film.

In general, the drug delivery device stents of Examples I-III were prepared with dioxane, chloroform or other solvents and different amounts of sirolimus (0-30%) and radiopaque agents (0-30%) having different particle sizes (0.1-10 microns). The films were prepared from PLGA 95/5 and PLGA 85/15. Once prepared, the films were laser cut into different lengths and geometries, i.e., solid ladder, open lattice & hybrid, wound on a mandrel at temperatures above the glass transition temperature of the polymers and then mounted onto balloon catheters and deployed in a water bath at 37° C. The solid ladder devices, with about 30% radiopaque agents, exhibited the greatest visibility, whereas the open lattice stents exhibited the lower visibility due to lesser mass of the open lattice stents. Referring back to FIG. 1, a solid ladder PLGA 95/5 stent 1a with 20% barium sulfate and 15% sirolimus is shown as balloon mounted 1b, and in its cut length 1c from the prepared film. The cut length 1c of the stent is 30 mm, the balloon mounted length 1b of the stent is about 20 mm, and the length of the deployed stent 1a is 18 mm. FIG. 3a-c shows similar length changes for the hybrid stent 3a in its film cut length 3c, its balloon mounted length 3b, and its deployed state 3a. The radial strength for the solid ladder stent 1a in FIG. 1a was about 20 to 25 psi, and the radial strength for the hybrid stent 3a of FIG. 3a was about 10 to 15 psi. The radial strength can be varied using amorphous or crystalline morphology, wherein amorphous stents will tend to have lower properties than crystalline stents.

As mentioned at different times herein, the bioabsorbable polymeric solution serving as the foundation of the film from which the drug delivery device will be cut from can be a blend of polymers as well as set forth in Example IV below.

Example IV

(a) Preparation of Films for Polymer Blend Evaluation

The intrinsic viscosity of PCL-PDO (95:5) and PGA-PCL (65:35) used in this study was about 1.5 and 1.4, respectively.

Films were cast in rectangular molds and dried in the original (single-sided) configuration. Films were dried first at 45° C. for 18 hours and then at 110° C. for 10 hours.

The solubility of the two softer copolymers in dioxane was assessed before preparation of the polymer blends. Solutions of PCL-PDO (95:5) and PGA-PCL (65:35) were prepared at a concentration of 6% by weight. The two solutions were first tumbled (7 revolutions/min) at room temperature overnight. After 24 h, PCL-PDO was completely dissolved while the PGA-PCL solution still contained free flowing granules. This solution was tumbled (5 revolutions/min) in an oven set at 60° C. After 1 hour of tumbling no granules remained.

The PGA-PCL solution was less viscous than PCL-PDO, which is less viscous than PLA-PGA (95:5) in dioxane at 6% by weight solids.

Pure films were prepared from PCL-PDO (95:5) as well as PGA-PCL (65:35) in dioxane. PGA-PCL formed a soft clear slightly brownish film while PCL-PDO formed an opaque and more brittle film.

The steps used to prepare the eight casting solutions (see Tables IV and V) are summarized below:

Blends of PLA-PGA (95:5) with 5%, 10%, 15% and 20% PGA-PCL (65:35)
- Weigh and add target mass of PLA-PGA into amber bottle. Next weigh and add target mass of PGA-PCL into amber bottle. The final polymer solids content was 6% w/w in dioxane.
- Weigh and add the target mass of dioxane directly into amber bottle containing polymer.
- Purge head-space with nitrogen gas and seal bottle. Tumble overnight (rotational speed=5/min) at 60±2° C.

Blends of PLA-PGA (95:5) with 5%, 10%, 15% and 20% PCL-PDO (95:5)
- Repeat the same procedure for preparing blends of PLA-PGA (95:5) with 5%, 10%, 15% and 20% PCL-PDO (95:5).

TABLE IV

Composition of Casting Solutions Used to Prepare PLA-PGA/PGA-PCL Blends

| Ingredient | Mass (g) | Composition (% w/w) |
|---|---|---|
| Sample Number 1 | | |
| PLA-PGA (95:5) | 11.41 | 5.70 |
| PGA-PCL (65:35) | 0.60 | 0.30 |
| Dioxane* (g) | 188.10 | 94.00 |
| Sample Number 2 | | |
| PLA-PGA (95:5) | 10.80 | 5.40 |
| PGA-PCL (65:35) | 1.21 | 0.60 |
| Dioxane | 188.00 | 94.00 |
| Sample Number 3 | | |
| PLA-PGA (95:5) | 10.19 | 5.09 |
| PGA-PCL (65:35) | 1.84 | 0.92 |
| Dioxane | 188.08 | 93.99 |
| Sample Number 4 | | |
| PLA-PGA (95:5) | 9.60 | 4.80 |
| PGA-PCL (65:35) | 2.40 | 1.20 |
| Dioxane | 188.00 | 94.00 |

TABLE V

Composition of Casting Solutions Used to Prepare PLA-PGA/PCL-PDO Blends

| Ingredient | Mass (g) | Composition (% w/w) |
|---|---|---|
| Sample Number 1 | | |
| PLA-PGA (95:5) | 11.41 | 5.70 |
| PCL-PDO (95:5) | 0.60 | 0.30 |
| Dioxane* (g) | 188.02 | 94.00 |
| Sample Number 2 | | |
| PLA-PGA (95:5) | 10.81 | 5.40 |
| PCL-PDO (95:5) | 1.21 | 0.60 |
| Dioxane | 188.05 | 94.00 |
| Sample Number 3 | | |
| PLA-PGA (95:5) | 10.21 | 5.10 |
| PCL-PDO (95:5) | 1.80 | 0.90 |
| Dioxane | 188.00 | 94.00 |
| Sample Number 4 | | |
| PLA-PGA (95:5) | 9.59 | 4.80 |
| PCL-PDO (95:5) | 2.40 | 1.20 |
| Dioxane | 188.01 | 94.00 |

PLA-PGA films were prepared by pouring the solutions of the filtered solutions in to a mold after allowing all the bubbles to escape. The films were allowed to dry in nitrogen followed by drying at 45° C. for 18 h and at 110° C. for 10 hours.

Mechanical Testing was conducted using the similar method described earlier.

A summary of the mechanical properties of the PLA-PGA film blends is reported as an average over at least three test specimens in Table VI.

Drugs or bioactive agents, as in earlier described examples, materials or blends, or other ratios of materials and blends, could be added.

Blends with PGA-PCL

Increasing the PGA-PCL content has a pronounced influence on the stress at yield values. Values decreased from 63 to 20 MPa in going from 5% to 20% PGA-PCL in the films. Thus, films become easier to stretch with increasing PGA-PCL content.

Stress at break values also showed a similar trend, decreasing from a high of 55 to 20 MPa with increasing PGA-PCL content in the matrix.

The modulus decreased with increasing PGA-PCL content in the matrix. Values decreased from 3638 to 1413 Mpa in going from 5% to 20% PGA-PCL in the matrix.

TABLE VI

Tensile Properties of PLA-PGA Film Blends Cast from Dioxane

| Sample | Stress at Yield (MPa) | Strain at Yield* (%) | Modulus* (Mpa) | Stress at Break (MPa) | Strain at Break* (%) | Toughness (MPa) |
|---|---|---|---|---|---|---|
| Blends of PLA-PGA (95:5) with PGA-PCL | | | | | | |
| 5% PGA-PCL | 62.9 | 3.68 | 3638 | 54.5 | 7.9 | 22.4 |
| 10% PGA-PCL | 55.5 | 3.75 | 3247 | 47.9 | 11.8 | 72.0 |
| 15% PGA-PCL | 28.7 | 3.39 | 1669 | 28.3 | 5.0 | 12.5 |
| 20% PGA-PCL | 20.4 | 2.90 | 1413 | 20.4 | 5.2 | 10.0 |
| Blends of PLA-PGA (95:5) with PCL-PDO | | | | | | |
| 5% PCL-PDO | 58.8 | 3.38 | 3537 | 57.4 | 4.2 | 14.9 |
| 10% PCL-PDO | 52.7 | 3.56 | 3189 | 45.9 | 8.6 | 33.8 |
| 15% PCL-PDO | 49.8 | 3.31 | 2956 | 49.3 | 3.3 | 10.3 |
| 20% PCL-PDO | 34.5 | 3.20 | 2057 | 34.4 | 3.2 | 5.0 |

*Strain at yield and strain at break as well as the modulus were calculated based on grip separation and not extensometer values.

Blends with PCL-PDO
The same trends were observed for blends of PLA-GA with PCL-PDO; however, the changes in the mechanical properties with increasing PCL-DO were less pronounced.
  Increasing the PCL-PDO content has a marked influence on the stress at yield values. Values decreased from 59 to 35 MPa in going from 5% to 20%
  PCL-PDO in the films. The change in the modulus is however less pronounced than with PGA-PCL.
  Stress at break values also showed a similar trend, decreasing from a high of 57 to 34 MPa with increasing PCL-PDO content in the matrix.
  The modulus decreased with increasing PCL-PDO content in the matrix. Values decreased from 3537 to 2057 Mpa in going from 5% to 20% PCL-PDO in the matrix.
(b) Plasticized Polymers Films Prepared from Dioxane
Blends of poly(lactic acid-co-glycolic acid) (PLA-PGA, 95:5) with three different grades of poly(ethylene glycol) (PEG 600, 1500 and 3442) at levels of 5%, 10% and 15% of total solids; and
Blends of poly(lactic acid-co-glycolic acid) (PLA-PGA, 95:5) with citrate ester, Citroflex® A-4 at levels of 5%, 10% and 15% of total solids.
Different grades of PEGs and citrate ester were obtained from Sigma Aldrich and Morflex, Inc., respectively.
  Twelve PLA-PGA casting solutions with various plasticizers at different levels were prepared in dioxane. The compositions of these solutions are summarized in Tables VII and VIII.
  The steps used to prepare these casting solutions are summarized below:
Blends of PLA-PGA (95:5) with 5%, 10% and 15% PEG
Weigh and add into amber bottle target mass of PLA-PGA.
Next weigh and add target mass of PEG plasticizer into amber bottle containing polymer.
The final PLA-PGA/plasticizer solids content is 6% w/w in dioxane.
Weigh and add target mass of dioxane directly into amber bottle containing PLA-PGA and plasticizer. Purge headspace with nitrogen gas and seal the bottle. Tumble overnight (rotational speed=5/min) at 60±2° C.
Blends of PLA-PGA (95:5) with 5%, 10% and 15% Citroflex® A-4
Repeat the procedure described above for preparing blends of PLA-PGA (95:5) with 5%, 10% and 15% Citroflex® A-4.

TABLE VII

Composition of Casting Solutions Used to Prepare PLA-PGA Films with Citroflex ® A-4 Plasticizer

| | Samples | | |
|---|---|---|---|
| Dioxane (g) | 188.04 | 188.06 | 188.05 |
| PLA-PGA (95:5) (g) | 11.42 | 10.81 | 10.21 |
| Citroflex ® A-4 (g) | 0.62 | 1.22 | 1.83 |
| Total mass (g) | 200.08 | 200.09 | 200.09 |
| Actual PLA-PGA (% w/w) | 5.71 | 5.40 | 5.10 |
| Actual Citroflex ® A-4 (% w/w) | 0.31 | 0.61 | 0.92 |
| Mass of casting solution poured into rectangular (5 × 7 in²) mold | 56 g | 56 g | 56 g |

TABLE VIII

Composition of Casting Solutions Used to Prepare PLA-PGA Films with PEG Plasticizer

| | Samples | | |
|---|---|---|---|
| Dioxane (g) | 188.02 | 188.00 | 188.04 |
| PLA-PGA (95:5) (g) | 11.40 | 10.82 | 10.20 |
| PEG 600 (g) | 0.60 | 1.20 | 1.84 |
| Total mass (g) | 200.02 | 200.02 | 200.08 |
| Actual PLA-PGA (% w/w) | 5.70 | 5.41 | 5.10 |
| Actual PEG 600 (% w/w) | 0.30 | 0.60 | 0.92 |
| Mass of casting solution poured into rectangular (5 × 7 in²) mold | 55 g | 55 g | 55 g |
| Dioxane (g) | 188.01 | 188.05 | 188.05 |
| PLA-PGA (95:5) (g) | 11.42 | 10.81 | 10.22 |
| PEG 1500 (g) | 0.60 | 1.22 | 1.80 |
| Total mass (g) | 200.03 | 200.08 | 200.07 |
| Actual PLA-PGA (% w/w) | 5.71 | 5.40 | 5.11 |
| Actual PEG 1500 (% w/w) | 0.30 | 0.61 | 0.90 |
| Mass of casting solution poured into rectangular (5 × 7 in²) mold | 55 g | 55 g | 55 g |
| Dioxane (g) | 188.03 | 188.05 | 188.02 |
| PLA-PGA (95:5) (g) | 11.41 | 10.83 | 10.24 |
| PEG 3442 (g) | 0.60 | 1.21 | 1.80 |
| Total mass (g) | 200.04 | 200.09 | 200.06 |
| Actual PLA-PGA (% w/w) | 5.70 | 5.41 | 5.12 |
| Actual PEG 3442 (% w/w) | 0.30 | 0.61 | 0.90 |
| Mass of casting solution poured into rectangular (5 × 7 in²) mold | 56 g | 56 g | 56 g |

PLA-PGA films were prepared by the same method as described earlier for the polymer blends and the mechanical properties of the films were determined.
Mechanical properties of films dried at 110° C. exhibited lower strain values due to phase separation between the polymer and the plasticizer. Due to this brittleness, the strain at break values reduced in the presence of the plasticizers induced by the 110° C. drying conditions. When the films were dried at 60° C., followed by supercritical carbon dioxide extraction, the extraction temperature was about 40° C. At 40° C. the films were not brittle. The strain at break values therefore increased with increasing amounts of plasticizers.
Helical stents were prepared from PLGA 85/15 with 20% barium sulfate and 10% sirolimus (similar to FIG. 6b). The films that were used to prepare the stents were prepared the same way as described above from dioxane. The main difference was the drying conditions. They were dried at 60° C. for 6 hours followed by supercritical carbon dioxide extraction of the residual solvent. This drying method provided more than 95% drug content in the stent. These stents were sterilized by ethylene oxide. Animal studies were conducted using this stent. It was observed that drug diffusion at the stented site approximated up to at least 30 mm distal and proximal of the stented site over varying time periods. For example, drug uptake in vessel tissue and drug elution pharmacokinetics is represented in the graphs shown in FIGS. 9 and 10.

Helical stents were also prepared from PLGA 85/15 blended with 10% PCL/PGA and contained 30% barium sulfate and 15% sirolimus. The films were prepared from dioxane and were also dried at 60° C. for 6 hours followed by supercritical carbon dioxide extraction of the residual solvent. Animal studies were also conducted using this stent.

Alternatively, the bioabsorbable polymeric materials and additives used to comprise the drug delivery device according to the systems and methods of the invention can be solvent cast as tubes as set forth in the following additional Examples V set forth below. In Examples V the devices are comprised of bioabsorbable polymeric materials, wherein the bioabsorbable materials are comprised of polylactide/polyglycolide copolymers such as PLA/PGA (95/5 and 85/15), and/or blends thereof. As discussed above, blends may render polymers more ductile and flexible while maintaining desired stiffness. Different solvents were used to prepare the tubes in the examples. The solvents included chloroform, dioxane, or binary solvent mixtures such as dioxane/acetone and dioxane/ethyl acetate. Different radiopaque materials were also used including barium sulfate, bismuth subcarbonate, bismuth oxide, tungsten and tantalum. The radiopaque materials were used in weights varying from 10 to 40% (by weight). Sirolimus was used as the drug in weights varying from 0 to 30% (by weight).

Figure 8:
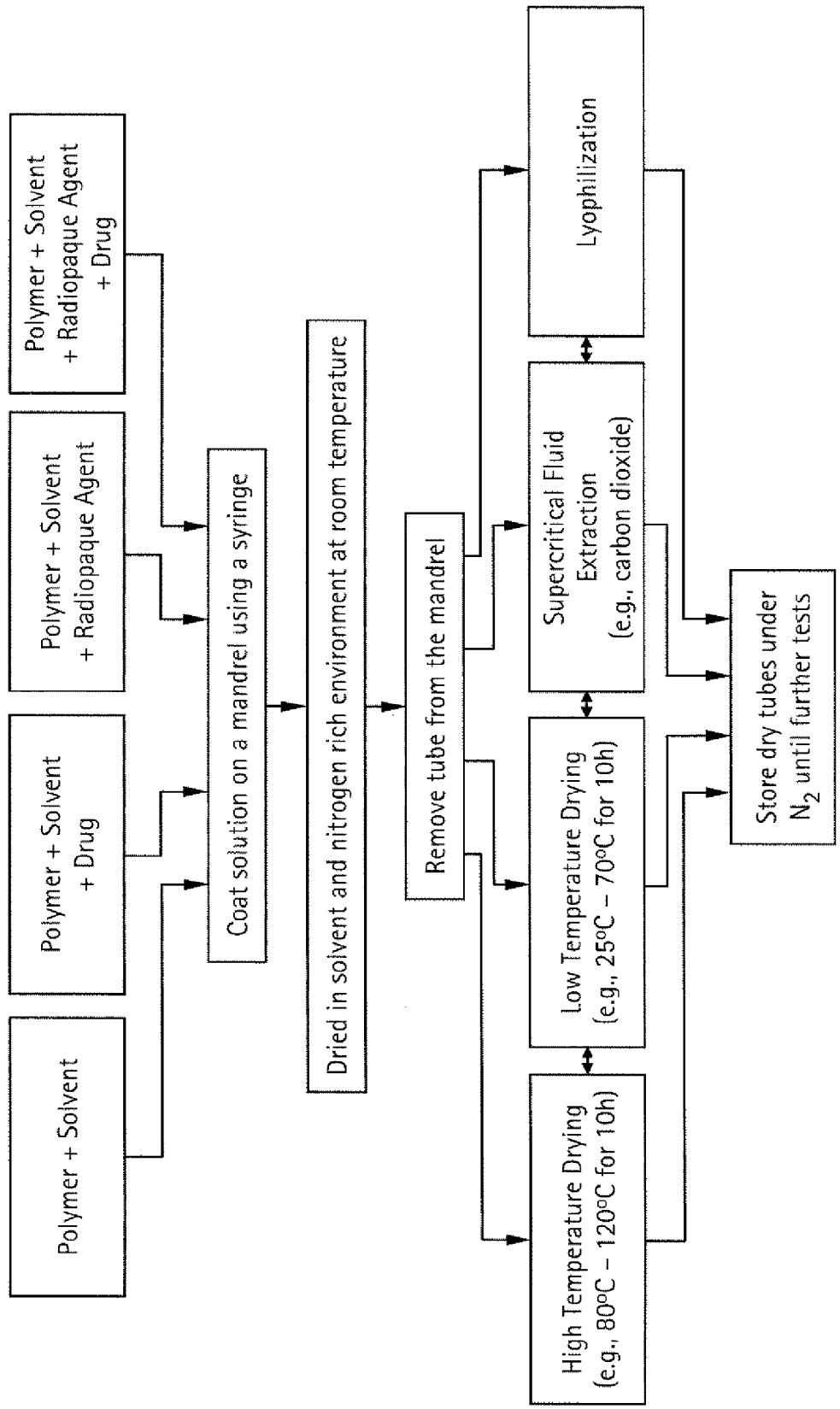
FIG. 8 illustrates a flow diagram of a tube fabrication process according to the systems and methods of the invention.

FIG. 8 shows schematically the solvent cast fabrication steps to form tubes. Polymer resins are added to a given solvent and tumbled with or without heat until the polymer dissolves completely in the solvent to provide a homogenous solution. Polymer formulations can be prepared using these solutions that may include radiopaque agents, drugs or combinations thereof. These formulations are tumbled and mixed to prepare uniform dispersions. The polymer solution is then deposited onto a mandrel at room or higher temperature. The deposition may occur at 12 mL/hour while the mandrel may revolve at 30 rpm. The mandrel may be coated, for example with Teflon, improve eventual removal therefrom. A syringe pump, for example, may be used to deposit the polymer solution onto the mandrel. The mandrel is then dried. The mandrel may be dried in a solvent rich environment and/or a nitrogen rich environment. The polymer tube is then removed from the mandrel and may be further dried under conditions including high temperature oven drying (e.g., 110° C. for 10 hours), low temperature oven drying (e.g., 25° C. to 60° C. for 6 hours), low temperature carbon dioxide extraction (e.g., 40° C. at 60 to 80 bar pressure for 20 to 60 minutes), lyophilization and combinations thereof. Low temperature drying is used to preserve drug content in the films. The drying conditions will also determine the morphology (amorphous or crystalline) of the tubes. After drying, the tubes can then be stored in an inert environment (nitrogen box) until further testing and prototyping.

Example V

Preparation of Polymer Tubes (PLA/PGA 95/5) with Sirolimus from Chloroform

The objective of the work was to develop methods for fabricating tubing out of a solution of biodegradable PLA/PGA copolymers in a solvent with varying sirolimus drug content. Tubes were prepared with drug loadings of 0, 5, 10, 15, and 30 wt % sirolimus. The solution was delivered to a Teflon coated mandrel at a set flow rate for a given drug concentration to give a continuous layer of solution of constant thickness, wherein the solution delivery rate decreases as the concentration of drug increases. The final thickness of the tube wall was determined by the solution concentration and the laydown rate of the solution onto the mandrel, which in turn is determined by the pumping rate and the mandrel speed. A solvent chamber is used to reduce the evaporation rate of the solvent from the coated mandrel so as to avoid bubble formation in the coating as it dries.

Exemplary specifications for the tubes were:

| Tube Parameter | Target |
|---|---|
| Inside diameter | 1 and 3.50 mm |
| Length | 25 mm |
| Wall thickness | 0.005 to 0.010 inches (127 to 2504 μm) |

The materials used were:

| Component | Amount | Percent |
|---|---|---|
| 95/5 PLA/PGA | 14.53 grams | 8.30% |
| Chloroform, Sigma-Aldrich, HPLC grade, water content less than 0.01% | 160.47 grams | 91.70% |

Drugs or bioactive agents may also be added as in earlier described examples.

The following processing conditions were used for Example V:

Prepare and provide an 8.3 wt % solution of the PLA/PGA & add drugs/agents as desired. (Sirolimus is added in appropriate amounts to this solution to prepare differing PLA/PGA polymer to drug ratios).

Set the apparatus conditions as follows:

Mandrel RPM=34.5

Position stage speed=4.11 cm/min

Set the solution dispense rate according to the amount of total solids in the solution formulation. (With no drug in the formulation the dispense rate is 38 mL/hour, whereas with 30% sirolimus the rate is 28 mL/hour. The rates are ideally calculated so as to give a consistent thickness (0.15 mm) of the dried tube.)

Provide chloroform solvent in the bottom of the solvent chamber to a depth of approximately 1 cm, place the mandrel into the solvent chamber, and then place the mandrel/solvent chamber into the apparatus.

Dispense the solution onto the mandrel using the conditions specified above. Full deposition is ideally achieved in one pass.

Rotate the coated mandrel in the solvent chamber for at least 45 additional minutes. (During this period, relatively little air flows over the solvent chamber so as to minimize the drying rate.)

Remove the coated mandrel from the solvent chamber and placed the mandrel in the nitrogen purge chamber for room temperature drying for at least 1.5 hours. The purge rate is fairly low (0.5 to 1 SCFH).

After initial drying, place mandrel into oven at 40°-60° C. for about 10 minutes.

Remove the mandrel from the oven and clamp one free end.

Break the adhesion of the tube on the mandrel by gently twisting sections of the tube.

Remove the tube from the mandrel by pushing the tube off of the mandrel.

Trim the ends of the tube and replace the tube onto the mandrel.

Place the mandrel and tube into the oven for further drying to remove residual solvents.

Remove the mandrel and tube from the oven and slip the tube off of the mandrel.

Store tubes in sealed vials until needed.

PLA/PGA (95:5) tubes having fairly constant wall thicknesses while containing various amounts of the drug sirolimus were produced as a result of the above process, as set forth in Table X below:

TABLE X

Summary of PLA/PGA (95:5) Tubes

| Sirolimus Content | Wall Thickness |
| --- | --- |
| none | ~0.15 to 0.18 mm (0.006" to 0.007") |
| 5% | ~0.15 to 0.16 mm (0.006") |
| 10% | ~0.15 to 0.17 mm (0.006" to 0.007") |
| 15% | ~0.18 mm (0.007") |
| 20% | ~0.15 to 0.18 mm (0.006" to 0.007") |
| 30% | ~0.15 mm (0.006") |

Example VI

Tubes Prepared from PLA/PGA (85/15) with Sirolimus from Chloroform

These PLA/PGA (85:15) tubes were prepared using similar steps as identified in Example V except with a mandrel condition of 31 RPM and a stage speed of 4.1 cm/min. As before, the solution delivery rate decreases as the sirolimus drug concentration increases so as to maintain a fairly uniform wall thickness in the tubes produced thereby.

The specifications for the tubes were:

| Tube Parameter | Target |
| --- | --- |
| Inside diameter | 1 and 3.50 mm |
| Length | 25 mm |
| Wall thickness | 0.005 to 0.006 inches (0.127 to 0.152 mm) |

The materials used were:

| Material |
| --- |
| 85/15 PLA/PGA copolymer |
| Chloroform, Sigma-Aldrich 99.9+ HPLC grade, 0.5% ethanol stabilizer, water content less than 0.01% |
| Sirolimus, refrigerated at 4° C. |

PLA/PGA (85:15) tubes having fairly constant wall thicknesses while containing various amounts of the drug sirolimus dispensed at various rates were produced as a result of the above process, as set forth in Table XI below:

TABLE XI

Summary of 85/15 PLA/PGA Tubes

| Sirolimus | Wall Thickness |
| --- | --- |
| None | 0.14 to 0.15 mm |
| 5% | 0.15 mm |
| 10% | 0.14 to 0.15 mm |
| 15% | 0.15 mm |
| 20% | 0.14 to 0.15 mm |
| 30% | 0.15 mm |

Example VII

Tubes Prepared from PLA/PGA 95/5 with Radiopaque Agents from Chloroform

Tubes were formed with PLA/PGA 95/5 copolymer and 10, 20, and 30 wt % $BaSO_4$ and $(BiO)_2CO_3$ as x-ray opacifiers for the tubes. The tube sizing specifications were the same as in Examples V & VI.

The following materials were used in the preparation of the tubes:

| Material |
| --- |
| 95:5 PLA/PGA copolymer |
| Chloroform, Sigma-Aldrich, 99.9+ HPLC grade, 0.5% ethanol stabilizer, water content less than 0.01% |
| Barium sulfate, $BaSO_4$ |
| Bismuth subcarbonate, $(BiO)_2CO_3$ |

The PLA/PGA material was received dry and stored under high vacuum prior to use. The chloroform was used as received.

The bismuth subcarbonate and barium sulfate were dried at 110° C. for 24 hours then stored under nitrogen prior to use.

Preparation

The apparatus and procedure for preparing the tubes was the same as described earlier with respect to Example V, wherein 10 wt % PLA/PGA (95:5) was used.

As the concentration of the radiopaque material increased the solution delivery rate decreased in order to maintain a uniform wall thickness of the tube. Because the density of the radiopaque materials is generally not as great as the density of the drug sirolimus, for instance, the delivery rate is generally not decreased as much as might occur to compensate for an increased drug concentration in the solution. Based on the preceding method the following radiopaque coating solutions were prepared:

These 10 wt % PLA/PGA (95:5) solutions with $BaSO_4$ or $(BiO)_2CO_3$ added thereto were then used to prepare tubes under the following conditions:

| Mandrel RPM | Dispenser Nozzle Speed (cm/min) | Solution Delivery Rate (mL/hour) |
| --- | --- | --- |
| 31 | 4.1 | 38 |
| 31 | 4.1 | 36 |
| 31 | 4.1 | 34 |
| 31 | 4.1 | 37 |
| 31 | 4.1 | 35.5 |
| 31 | 4.1 | 35.5 |

The stent tubes were dried as above.

Radiopaque Tube Samples Prepared

A list of the sample tubes prepared is shown in Tables XII and XIII, wherein the tubes were thereafter packed in vials and sealed until desired.

TABLE XII $BaSO_4$ Sample Tubes

| $BaSO_4$ Amount in Solids | Wall Thickness |
| --- | --- |
| 10% | 0.16 to 0.17 mm |
| 20% | 0.15 to 0.17 mm |
| 30% | 0.15 mm |

TABLE XIII $(BiO)_2CO_3$ Sample Tubes

| $(BiO)_2CO_3$ in Solids | Sample Wall Thickness |
| --- | --- |
| 10% | 0.14 to 0.15 mm |
| 20% | 0.15 mm |
| 30% | 0.15 mm |

Similar tubes were prepared from PLA/PGA 85/15 with 30% barium sulfate; and with 30% barium sulfate and PCL/PGA blend from dioxane.

The various bioabsorbable polymers, blends, drugs, bioactive agents and solvent described herein may be used to fabricate tubes according the systems and methods as described herein.

The bioabsorbable materials used to form the drug delivery device are chosen as discussed herein in order to achieve the desired flexibility, mechanical integrity, degradation rates, shape, geometry and pattern of the device. Plasticizers can be added to the matrix of bioabsorbable polymer materials, if desired, in order to render the device even more flexible. The plasticizers are added to the bioabsorbable materials of the device prior to or during processing thereof. The plasticizers are preferably materials of lower molecular weight than the bioabsorbable materials that are being processed to comprise the device. Adding the plasticizers renders the bioabsorbable materials more flexible and typically reduces processing temperatures. As a result, degradation of drugs incorporated into the bioabsorbable materials having plasticizers added thereto during processing is further minimized. Melt extrusion temperatures can also be lowered by adding different solvents to the polymer before or during extrusion. Blends of polymers, with melting points lower than the melting point of the bioabsorbable materials in which the drugs or other bio-active agents are to be incorporated, may also be added to the bioabsorbable materials that are to comprise the device. Adding the blends of polymers having the lower melting points also helps to reduce processing temperatures and minimize degradation of the drugs or agents thereby.

In the case of a stent device comprised of bioabsorbable materials formed by co-extrusion, different bioabsorbable polymeric materials may be used whereby the different polymer tubes are extruded generally at the same time to form a sheath and a core, respectively, of the stent. Bioabsorbable polymeric materials having low melting points are extruded to form the sheath or outside surface of the stent. These low melting point materials will incorporate the drugs or other bio-active agents for eventual delivery to the patient, whereas materials having higher melting points are extruded to form the core or inside surface of the stent that is surrounded by the sheath. The higher melting point materials comprising the core will thus provide strength to the stent. During processing, the temperatures for extruding the low melting point drug containing materials (e.g., polycaprolactone and/or polydioxanone) can be as low as 60° C. to 100° C. Further, because the drugs or other bio-active agents added to the devices made by this co-extrusion method tend to be coated onto the device after the device has been extruded, the drugs or agents are not exposed to the high temperatures associated with such methods. Degradation of the drugs during processing is minimized therefore. Because the co-extrusion of different tubes requires fairly precise co-ordination, stents of simpler shapes tend to be formed using this co-extrusion method. Radiopaque agents may be incorporated into the device during or after extrusion thereof.

In the case of a stent device comprised of bioabsorbable polymeric materials formed by co-mingled fibers, different bioabsorbable polymeric materials may also be used.

Contrary to the co-extrusion techniques described above, the co-mingled fibers technique requires that each fiber be separately extruded and then later combined to form a stent of a desired geometry. The different bioabsorbable polymeric materials include a first fiber having a low temperature melting point into which a drug is incorporated, and a second fiber having a higher temperature melting point. As before, radiopaque agents may be added to one or more of the fibers during, or after, extrusion thereof.

In the case of a stent comprised of bioabsorbable materials formed by supercritical fluids, such as supercritical carbon dioxide, the supercritical fluids are used to lower processing temperatures during extrusion, molding or otherwise conventional processing techniques. Different structures, such as fibers, films, or foams, may be formed using the supercritical fluids, whereby the lower temperature processing that accompanies the supercritical fluids tends to minimize degradation of the drugs incorporated into the structures formed.

Drug delivery devices or stents, as described herein, may also be made with or without drugs, agents or radiopaque materials added thereto as from compression molded films, for example. In the case of devices made from compression molded films, PLLA, PLGA (85/15), PLGA (95/5) or other bioabsorbable materials may be used. Once prepared the films are cut into film strips of lengths as desired and converted to a geometry as desired. Where the film strips are to be converted into helical coil stents such as shown in FIGS. 1-3, the strips, once cut, are placed onto a heated mandrel and heated to above the glass transition temperature of the polymer. Lower profile stents may be achieved by using a mandrel with a smaller outer diameter. The helical coiled strips are then transferred to a balloon catheter and nested at different pressures (200-220 psi) and temperatures (60-100° C.) using nesting tubes (e.g., 0.0067 mils) in order to achieve stepwise reductions in the stent diameter. Thereafter, the nested stents are deployed in a water bath at 37° C. at nominal pressures (8-12 psi) in silicon tubings. Radial strength of such stents formed from compression molded films varies depending on the geometry or design of the device and the wall thickness.

While the above described systems and methods of the invention have focused primarily on stent devices comprised of bioabsorbable polymeric materials with drugs and radiopaque materials added thereto, the artisan will appreciate that devices other than stents may as well be comprised of bioabsorbable materials with drugs and radiopaque materials according to the systems and methods of the invention. As with stents, the devices may take on different geometries according to the techniques used to form the devices, whereby melt compounded blends of bioabsorbable materials, drugs and radiopaque materials may be melt spun into fibers, compression molded into discs or rings, extruded into tubes or injection molded into more intricate devices. Solution processing may instead be used to form the non-stent devices whereby super critical fluids, such as carbon dioxide, or other solvent extraction, extrusion or injection molding techniques may also be used to minimize degradation of the drugs or other agents by reducing the processing temperature to which the bioabsorbable materials are subjected.

As with the earlier described stent drug delivery devices, different geometries of non-stent drug delivery devices formed by the various processes can also be achieved. After processing, the fibers, tube, films, discs, rings, or other geometry of the non-stent devices may be laser cut and/or braided into a desired shape or pattern.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A method of forming a drug delivery device, the method comprising:
   adding at least one polymer resin to a solvent until the polymer dissolves completely in the solvent to form a first polymer solution;
   adding at least one polymer resin to a solvent until the polymer dissolves completely in the solvent to form a second polymer solution;
   co-extruding a first bioabsorbable polymer tube having a first melting point from the first solution and a second bioabsorbable polymer tube having a second melting point from the second solution at the same time to form a coaxial sheath and core, respectively, of a stent having luminal and abluminal surfaces, wherein the first melting point is lower than the second melting point.

2. The method of claim 1, wherein the sheath comprises at least one of polycaprolactone and polydioxanone.

3. The method of claim 1, further comprising coating the drugs or bioactive agents onto the device after extrusion thereof.

4. The method of claim 1, further comprising incorporating radiopaque materials into, or onto, the device.

5. The method of claim 1 wherein the first bioabsorbable polymer tube comprises a material having a low melting point.

6. The method of claim 5 wherein the melting point is between approximately 60° C. to about 100° C.

7. The method of claim 1 wherein the first bioabsorbable polymer tube comprises at least one drug or other bioactive agent.

8. The method of claim 7 wherein the at least one drug or other bioactive agent is incorporated into the polymer matrix by adding the at least one drug or other bioactive agent and the first bioabsorbable polymer together in a solution until the at least one drug or other bioactive agent and the first bioabsorbable polymer dissolve completely in the solvent to form a homogenous solution.

9. The method of claim 1 wherein the second bioabsorbable polymer tube comprises at least one drug or other bioactive agent.

10. The method of claim 9 wherein the at least one drug or other bioactive agent is incorporated into the polymer matrix by adding the at least one drug or other bioactive gent and the second bioabsorbable polymer together in a solution until the at least one drug or other bioactive agent and the second bioabsorbable polymer dissolve completely in the solvent to form a homogenous solution.

11. The method of claim 4 wherein the radiopaque material is incorporated into the polymer matrix of the first bioabsorbable polymer tube.

12. The method of claim 4 wherein the radiopaque material is coated over at least a portion of the first bioabsorbable polymer tube.

13. The method of claim 1 wherein the bioabsorbable polymer tube comprising a material having a high melting point to provide strength.

* * * * *